United States Patent [19]
Ziegler, Jr. et al.

[11] Patent Number: 5,480,987
[45] Date of Patent: Jan. 2, 1996

[54] 2-SUBSTITUTED ALKYL-3-CARBOXY CARBAPENEMS AS ANTIBIOTICS AND A METHOD OF PRODUCING THEM

[75] Inventors: Carl B. Ziegler, Jr.; William V. Curran, both of Pearl River; Gregg Feigelson, Spring Valley, all of N.Y.

[73] Assignee: American Cyanamid Company, Wayne, N.J.

[21] Appl. No.: 234,905

[22] Filed: Apr. 28, 1994

Related U.S. Application Data

[62] Division of Ser. No. 87,944, Jul. 6, 1993, Pat. No. 5,369,102, which is a continuation of Ser. No. 749,019, Aug. 23, 1991, abandoned, which is a division of Ser. No. 507,271, Apr. 10, 1990, Pat. No. 5,068,232.

[51] Int. Cl.$^6$ .......................... C07D 205/08; C07F 7/18; A61K 31/40
[52] U.S. Cl. .......................................................... 540/200
[58] Field of Search ............................................. 540/200

[56] References Cited

U.S. PATENT DOCUMENTS

| | | | |
|---|---|---|---|
| 4,350,631 | 9/1982 | Christensen | 546/272 |
| 4,377,591 | 3/1983 | Hiraoka | 424/274 |
| 4,845,210 | 7/1989 | Nakai | 540/200 |

FOREIGN PATENT DOCUMENTS

| | | |
|---|---|---|
| 79798-82 | 1/1982 | Australia . |
| 54917 | 1/1981 | European Pat. Off. . |
| 0171064 | 2/1986 | European Pat. Off. . |
| 240164 | 2/1986 | European Pat. Off. . |
| 0184844 | 6/1986 | European Pat. Off. . |
| 282241 | 3/1987 | European Pat. Off. . |
| 0265117 | 4/1988 | European Pat. Off. . |
| 0366143 | 10/1989 | European Pat. Off. . |
| 0481116 | 4/1992 | European Pat. Off. . |
| 58-103388 | 6/1983 | Japan . |
| 193586 | 4/1989 | Japan . |
| 199487 | 2/1986 | New Zealand . |
| 2071656 | 9/1981 | United Kingdom . |
| 2196340 | 10/1987 | United Kingdom . |
| 2092147 | 8/1992 | United Kingdom . |

OTHER PUBLICATIONS

J. Tsuji, Tetrahedron Letters (1980), vol. 21 pp. 849–850.
H. Hofmeister, Ang. Chem. Int. Ed. Engl. (1984) vol. 23 pp. 727–728.
K. Hartke, Tetrahedron Letters (1989), vol. 30, No. 9, pp. 1073–1076.
T. Kobayashi, Chemistry Letters (1987) pp. 1209–1212.
R. F. Newton, Tetrahedron Letters (1979), No. 41, pp. 3981–3982.
R. N. Guthikonda, J. Med. Chem. (1978), vol. 30 pp. 871–880.
T. N. Salzmann, "Recent Advances In The Chemistry Of Bata–Lactam Antibiotics", 1989 pp. 171–189.
de Vries, Tetrahedron Letters, vol. 25, No. 52 pp. 5989–5992 (1984).
de Vries, Heterocycles, vol. 23, No. 8 pp. 1915–1919 (1985).
T. W. Greene, "Protective Groups In Organic Synthesis", 1981 pp. 88–101, 223–249, 195–213.
A. Hassner, Tetrahedron Letters, No. 46, pp. 4475–4478.
W. E. Truce, J. Organic Chemistry 1971, col. 36, No. 13, pp. 1727–1731.
S. Patai, "The Chemistry Of The Carbon–Carbon Triple Bond", J. Wiley (1978) pp. 320–327.
S. Uemura, J. Chem. Soc. Chem. Commun. (19750 pp. 925–926.
L. Brandsma, "Preparative Acetylenic Chemistry", Elsevier (1988) Chapter 8.
J. March, "Advanced Organic Chemistry", J. Wiley, 3rd Ed (1985) pp. 295–296.
M. Ohtani, "Mild Deprotection Of Carbapenm Esters With Aluminum Trichlorids", J. Organic Chem (1984), 49, 5271–5272.
Chemical Abstracts, vol. 99 No. 17, 24th Oct. 1983, p. 572, abstract No. 139645b & JP–A–58 103 388.
Chemical Abstracts, vol. 104, No. 1, 6th Jan. 1986, p. 516, abstract No. 5672w, and Heterocycles 1985, 23(8), 1915–19.
Tetrahedron Letters, vol. 28, No. 25, 1987, pp. 2887–2888.

*Primary Examiner*—Mark L. Berch
*Attorney, Agent, or Firm*—T. S. Szatkowski

[57] ABSTRACT

The invention provides substituted allylazetidinone compounds having the formula:

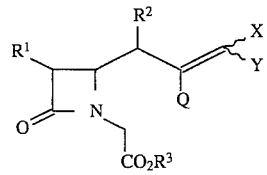

Formula XVII and propargyl azetidinone compounds having the formula:

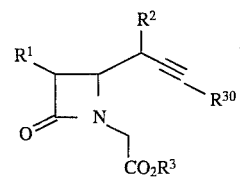

wherein $R^1$, $R^2$, $R^3$, $R^{30}$, X, Y and Q are defined in the specification.

23 Claims, No Drawings

2-SUBSTITUTED ALKYL-3-CARBOXY CARBAPENEMS AS ANTIBIOTICS AND A METHOD OF PRODUCING THEM

This is a divisional of copending application(s) Ser. No. 08/087,944 filed on Jul. 6, 1993 now U.S. Pat. No. 5,369,102; which is a continuation of application Ser. No. 07/749,019 filed Aug. 23, 1991 and now abandoned; which is a divisional of application Ser. No. 07/507,271, filed Apr. 10, 1990 now U.S. Pat. No. 5,068,232.

BACKGROUND OF THE INVENTION

1. Field of the Invention

The invention relates to new 2-substituted alkyl-3-carboxy carbapenems having the formula:

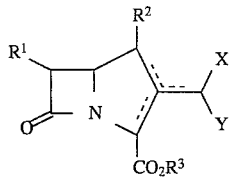

with $R^1$, $R^2$, $R^3$, X and Y defined hereafter as antibiotics and beta lactamase inhibitors produced by a novel Michael addition-elimination reaction of a substituted allyl azetidinone in the reaction shown:

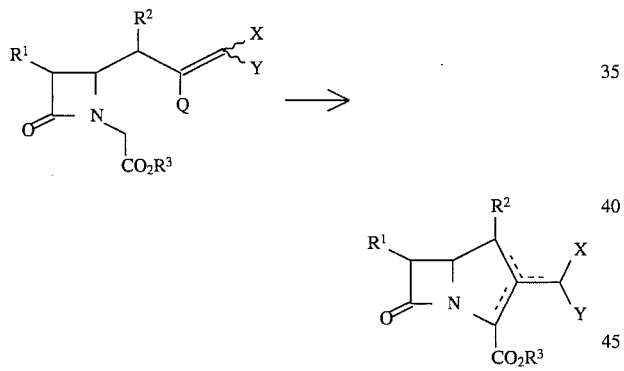

with $R^1$, $R^2$, Q, X and Y defined hereafter

2. Description of the Prior Art

2-Substituted alkyl-3-carboxy carbapenems are known to be effective antibiotics. For example, T. N. Salzmann et. al. in "Recent Advances in the Chemistry of β-Lactam Antibiotics" P. H. Bentley and R. Southgate eds., Royal Society of Chemistry, 1989, pp 171–189 discloses carbapenems of this type as having antibacterial activity.

Sandoz reported in *Tetrahedron Letters*, Vol. 25, No. 52, pp. 5989–5992 (1984) the intermolecular Wittig reaction between 2-oxocarbapenem-3-carboxylic esters and triphenylphosphorane ylides as shown gives exo and endo

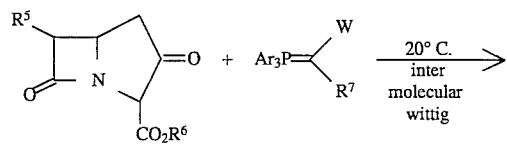

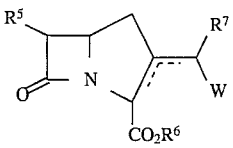

mixtures of product (dotted lines represent mixtures of endocyclic and exocyclic double bonds) wherein W=CN, $CO_2CH_3$ and $COCH_3$ and $R^7$=H, $R^5$=ethyl or fluoroethyl and $R^6$ is either an ester group or a cationic species.

In EP 0265 117, published April 4, 1988, the same method of 2-alkyl-3-carboxy carbapenem synthesis using Wittig methodology is disclosed. In this disclosure V=CN, $COR^8$ or $CO_2R^8$; $R^8$ is $C_1$–$C_4$ alkyl, $C_7$–$C_{11}$ araalkyl; $R^9$=H, $C_1$–$C_4$ alkyl; $R^{10}$=hydroxyethyl or protected hydroxyethyl; $R^{11}$= ester protecting group.

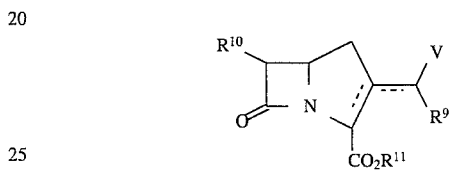

Stated in both publications was that the intermolecular Wittig reaction method gave much higher yields over the conventionally used intramolecular approach shown below (where W, $R^{10}$ and $R^{11}$ have the same distinction as before) and therefore was the method of choice.

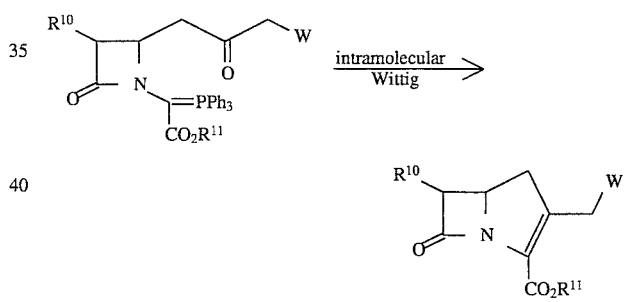

The selection of $R^7$ and $R^9$ in these disclosures is limited to H or C-substitution. Other substituents at this position such as halogens, i.e., chlorine would not be tolerated in either reaction mode (inter or intramolecular Wittig reaction). Indeed, a comprehensive literature search reveals no report of a triarylphosphorane species with general structure shown where $W^1$ has the same designation as W and V before and Z=halogen (F, Cl, Br, I).

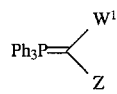

Thus, it is highly unlikely that 2-haloalkyl-3-carboxyl carbapenems could be prepared by Wittig methodology. However, such compounds can be prepared by the intramolecular Michael addition-elimination method of this invention.

In Japanese Patent Application No. 58-103,388 (Sankyo) published Jun. 20, 1983, carbapenems of the formula shown below are prepared via an intramolecular Wittig reaction where B, A and $R^{12}$

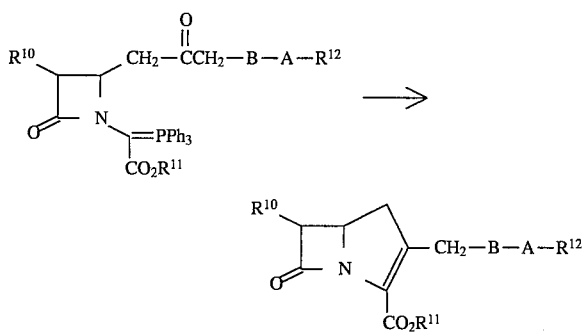

have the following designation: B is thio, sulfinyl, or sulfonyl; A is either a single bond or a linear or branched-chain alkylene; $R^{12}$ is a cyclic amine residue that forms a 3- to 8-membered ring overall and may include within the ring an oxygen, nitrogen, sulfur, sulfinyl, sulfonyl, or carbonyl, which nitrogen may be substituted with a lower aliphatic acyl that may have an amino group, lower alkyl-monosubstituted amino- or lower alkyl-disubstituted aminoalkylene, or a group of the formula

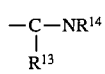

(wherein $R^{13}$ is hydrogen, amino, or a lower alkyl; and $R^{14}$ is hydrogen or a lower alkyl), in addition to which a group of the formula

(wherein $R^{15}$ is hydrogen or lower alkyl) present on the acyl or alkyl substituent on said cyclic amine residue may be replaced with a group having the formula

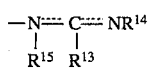

(wherein $R^{13}$, $R^{14}$ and $R^{15}$ have the same meaning as above).

The Sankyo disclosure provides no teaching or suggestion on the preparation of novel exocyclic double bond isomers shown below.

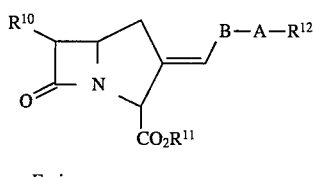

E - isomer

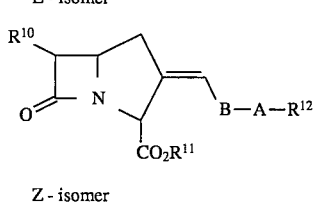

Z - isomer

By the Sankyo method of ring closure (intramolecular Wittig reaction) neither the E nor Z exoproduct isomers are possible, only endocyclic double bond isomers. These two exo isomeric products can be produced by the method involving the Michael-addition-elimination sequence disclosed in this invention. Additionally, the Sankyo disclosure provided no in vitro antibacterial activity data.

In Heterocycles, Vol. 23, No. 8, pp. 1915–1919 (1985) the Sandoz group reported a 2-alkyl-3-carboxy carbopenem shown via an intramolecular Wittig reaction

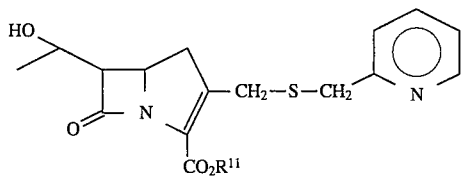

No antibacterial data of this carbapenem is provided in the disclosure.

It is an object of this invention to provide novel families of carbapenem antibiotics via a new and general chemical process that utilizes a Michael addition-elimination reaction of substituted allyl azetidinone intermediates. These intermediates also comprise a new and useful form of carbapenem precursor.

SUMMARY OF THE INVENTION

It has now been found that 2-substituted alkyl-3-carboxy carbapenems of the formula:

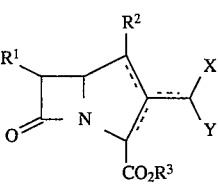

Formula I exhibit activity as an antibiotic and a β-lactamase

In the above Formula I, $R^1$ is hydrogen; straight-chain or branched lower alkyl group such as methyl, ethyl, n-propyl, isopropyl, n-butyl, isobutyl, sec-butyl, tert-butyl, n-pentyl, or isopentyl; straight-chained or branched lower alkoxy group such as methoxy, ethoxy, n-propoxy, isopropoxy, n-butoxy, isobutoxy, sec-butoxy, or tert-butoxy or an $R^4$ B group [wherein $R^4$ is a hydroxyl group; a lower alkoxy group such as methoxy, ethoxy, n-propoxy, or isopropoxy; fluoride; an acyloxy group such as a lower aliphatic acyloxy group (e.g., acetoxy, propionyloxy, n-butyryloxy, or isobutyryloxy) or an aralkyloxycarbonyloxy group (e.g., benzyloxycarbonyloxy or p-nitrobenzyloxycarbonyloxy); a lower alkylsulfonyloxy group such as methanesulfonyloxy, ethanesulfonyloxy, or propanesulfonyloxy; an arylsulfonyloxy group such as benzenesulfonyloxy or p-toluenesulfonyloxy; a lower trialkylsilyloxy group such as trimethylsilyloxy or tert-butyldimethylsilyloxy a mercapto group; a lower alkylthio group such as methylthio, ethylthio, n-propylthio, or isopropylthio an amino group; or a lower aliphatic acylamino group such as acetylamino, propionylamino, n-butyrylamino, or isobutyrylamino; and B is an alkylene group that may have trifluoromethyl or phenyl substituents, such as methylene, ethylene, ethylidene, trimethylene, propylidene, isopropylidene, tetramethylene, butylidene, pentamethylene, pentylidene, 2,2,2-trifluoroethylidene, 3,3,3-trifluoropropylidene, or benzylidene;

$R^2$=H, or substituted by substituent groups previously disclosed for other carbapenem derivatives. More specifically, $R^2$ may be hydrogen or any of the non-hydrogen 1-substituents disclosed for example, in European Patent Application No. 54,917 (see definition of $R^1$ or $R^2$ therein) or in U.S. Pat. No. 4,350,631. Preferred non-hydrogen $R^2$ substituents include ($C_1$–$C_6$) alkyl, most preferably, methyl, phenyl and phenyl ($C_1$–$C_6$) alkyl. The non-hydrogen $R^2$ substituent may be in either α- or β-configuration, and it is intended that the present invention include the individual α- and β-isomers, as well as mixtures thereof. The most preferred 1-substituted compounds are those having the β-configuration, especially those having the β-methyl substituent;

$R^3$ is a hydrogen atom; a straight-chain or branched lower alkyl group such as methyl, ethyl, n-propyl, isopropyl, n-butyl, isobutyl, or tert-butyl; a lower haloalkyl group such as 2-iodoethyl, 2,2-dibromoethyl, or 2,2,2-trichloroethyl; a lower alkoxymethyl group such as methoxymethyl, ethoxymethyl, n-propoxymethyl, isopropoxymethyl, n-butoxymethyl, or isobutoxymethyl; a lower aliphatic acyloxymethyl group such as acetoxymethyl, propionyloxymethyl, n-butyryloxymethyl, isobutyryloxymethyl, or pivaloyloxymethyl; a 1-(lower alkoxy)carbonyloxyethyl group such as 1-methoxycarbonyloxyethyl, 1-ethoxycarbonyloxyethyl, 1-n-propoxycarbonyloxyethyl, 1-isopropoxycarbonyloxyethyl, 1-n-butoxycarbonyloxyethyl, or 1-isobutoxycarbonyloxyethyl; an aralkyl group such as benzyl, p-methoxybenzyl, o-nitrobenzyl, or p-nitrobenzyl; a benzhydryl group; a phthalidyl group, a silyl such as trimethylsilyl or t-butyldimethylsilyl or 2-trimethylsilylethyl; allylic group such as allyl, 2-chloro-2-propenyl, 2-butenyl, 3-methyl-2-butenyl or 2-cinnamyl or water soluble cation such as lithium, sodium, potassium, ammonium or tetraalkyl ammonium (alkyl of $C_1$–$C_4$);

X=F, Cl, Br, I, H;

Y=$CO_2H$, $CO_2R^{16}$,

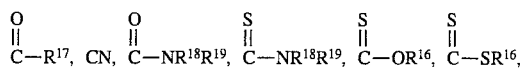

$SO_2R^{17}$, $SOR^{17}$, $SR^{17}$, F, Cl, Br, I, provided however that when Y=$CO_2R^{16}$,

CN, then X cannot be H.

$R^{16}$=a straight-chain or branched lower alkyl group such as methyl, ethyl, n-propyl, isopropyl, n-butyl, isobutyl; a lower haloalkyl group such as 2-chloroethyl, 3-chloropropyl, 2-iodoethyl, 2,2-dibromoethyl or 2,2,2-trichloroethyl; a lower trimethylsilylalkyl group such as 2-trimethylsilylethyl; substituted allyl (2-propenyl), 2-chloro-2-propenyl, 3-methyl-2-propenyl, 3-methyl-2-butenyl, 3-phenyl-2-propenyl; a lower alkyl-t-butyldimethylsiloxy group of 2–4 carbon atoms such as 2-[t-butyldimethylsiloxy]ethyl or 2-[t-butyldimethylsiloxy]propyl; a lower alkylhydroxy group of 2–4 carbon atoms such as 2-hydroxyethyl, 3-hydroxylpropyl or 3-hydroxy-n-butyl; aryl such as phenyl; alkylheteroaryl groups with 1–3 carbon atoms in the alkyl chain attached to a 5- or 6-membered heteroaryl ring that contains 1-4 O, N or S atoms attached through a ring carbon or nitrogen such as thienyl, furyl, thiadiazolyl, oxadiazolyl, triazolyl, isothiazolyl, thiazolyl, imidazolyl, isoxazolyl, tetrazolyl, oxazolyl, pyridyl, pyrazinyl, pyrimidinyl, pyrrolyl or pyrazolyl are preferred: alkylheterocycle groups with 1–3 carbon atoms in the alkyl chain attached to a 5- or 6-membered ring that contains 1–4 O, N or S atoms through a ring carbon or ring nitrogen such as morpholinyl, thiomorpholinyl, piperazinyl, piperidyl, pyrazolinyl, pyrazolidinyl, imidazolinyl, pyrrodinyl or pyrrolidinyl;

$R^{17}$=1) phenyl ring, optionally substituted by 1–3 substituents independently selected from; 1a) halogens (F, $C_1$, Br, I) and/or trifluoromethyl; 1b) $C_1$–$C_4$ branched or linear alkyl; 1c) hydroxy or protected hydroxy group, amino or protected amino group, thiol or protected thiol group (examples of commonly used phenyl-amino, -hydroxy and -thiol protecting groups are found in T. Greene, "Protective Groups in Organic Synthesis", J. Wiley & Sons, 1981, pp 88–101, 223–249 and 195–213, respectively); 1d) alkenyl and alkynyl groups having 1–4 carbon atoms such as ethenyl, 1-propenyl, 2-propenyl, 3-propenyl, ethynyl, 1-proynyl; 1e) carboxy or carboxamido groups; 1f) 5- or 6-membered heteroaryl rings that contain 1–4 O, N or S atoms attached through a ring carbon or nitrogen (if applicable) such as thienyl, furyl, thiadiazolyl, oxadiazoyl, triazoyl, imidazolyl, isoxazolyl, tetrazolyl, oxazolyl, pyridyl, pyrazinyl, pyrimidinyl, pyrrolyl or pyrazolyl are preferred; 1g) heterocycle groups that contain 1–4 O, N or S atoms attached through a ring carbon or nitrogen (if applicable) such as morpholinyl, thiomorpholinyl, piperazinyl, piperidyl, pyrazolinyl, pyrazolidinyl, imidazolinyl, pyrrolinyl, pyrrolidinyl, tetrahydrofuranyl, tetrahydropyranyl or tetrahydrothiophenyl;

2) fused phenyl ring, optionally one that is fused to a 5- or 6-membered heteroaryl ring containing 1–3 O, N or S atoms such as quinolinyl, isoquinolinyl, benzofuranyl, benzothiazolyl, benzoimidazolyl, benzothienyl, benzopyrazinyl;

3) 5- or 6-membered heteroaryl-rings that contain 1–4 O, N or S atoms attached through a ring carbon such as thienyl, furyl, thiadiazolyl, oxadiazoyl, triazolyl, isothiazolyl, thiazolyl, imidazolyl, isoxazolyl, tetrazolyl, oxazolyl, pyridyl, pyrazinyl, pyrimidinyl, pyrrolyl or pyrazolyl are preferred. Such aromatic heterocyclic rings may, where possible be fused to another unsaturated ring preferably a phenyl ring or a 5- to 6-membered saturated or unsaturated heterocyclic ring containing 1–3 O, N or S atoms;

4. Groups in catagories (2) and (3) above substituted, where possible, by 1–3 substituents independently selected from subcatagories 1a) through 1e). $R^{18}$ and $R^{19}$ are independently selected from hydrogen; substituted or unsubstituted alkyl having from 1–10 carbon atoms; substituted or unsubstituted cycloalkyl having from 1–10 carbon atoms, aralkyl, such as phenyl alkyl and heterocycloalkyl wherein the alkyl has 1–6 carbon atoms and the heteroatom or atoms are selected from O, N and S, and cyclic group wherein $R^{18}$ and $R^{19}$ are joined; and wherein the ring or chain substituent or substituents on $R^{18}$, $R^{19}$ or the cyclic radical formed by their joinier are selected from the group consisting of amino, mono, di- and trialkylamino (each alkyl having 1–6 C atoms), hydroxyl, carboxyl, alkoxyl having from 1–6 carbon atoms, halo such as chloro, bromo, fluoro, nitro, sulfonamido, phenyl, benzyl and alkoxylcarbonyl having 1–3 carbon atoms in the alkoxy moiety.

Relative to the above generic description for $R^{18}$, $R^{19}$ the following examples are representative for the 3-substituent $-NR^{18}, R^{19}$:

$-NH_2$, $-NHCH_3$, $-NHCH_2CH_3$, $-NHCH(CH_3)_2$, $-N(CH_3)_2$, $-N(CH_2CH_3)_2$, $-N[CH(CH_3)_2]_2$, $-NHCH_2CH_2OH$, $-NHCH_2CH_2CH_2OH$, $-N(CH_2CH_2OH)_2$, $-N[CH(CH_3)CH_2OH]_2$, $-NH(CH_2CO_2CH_3)$, $-NH(CH_2CH_2CO_2CH_3)$, $-NHCH_2CF_3$, $-NHCH_2CH_2NHCO_2C(CH_3)_3$, $-NHCH(CH_3)CH_2CO_2C(CH_3)_3$, $-NHCH_2CH_2NH_2$, $-NHCH_2CH_2N(CH_3)_2$, $-NHCH(CH_3)CH_2N(CH_3)_2$, $-NHNHCH_3$, $NHN(CH_3)_2$, $N(CH_3)NHCH_3$, $-N(CH_3)N(CH_3)_2$.

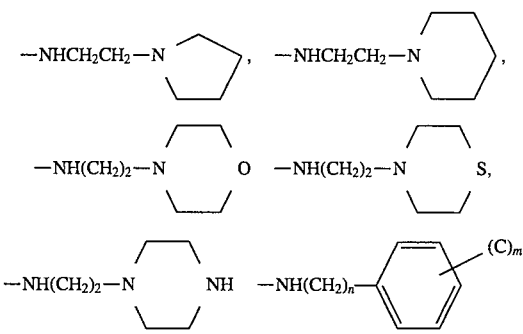

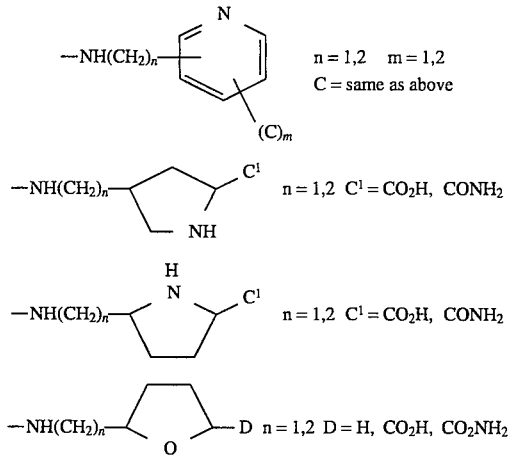

n = 1,2 m = 1,2
C = CH₃, OCH₃, Cl, Br, F, I, NO₂, OH
SO₂NH₂, CO₂H, CONH₂ n = 1,2 m = 1,2
C = same as above n = 1,2 C¹ = CO₂H, CONH₂ n = 1,2 C¹ = CO₂H, CONH₂ n = 1,2 D = H, CO₂H, CO₂NH₂

D = H, CO₂H, CONH₂

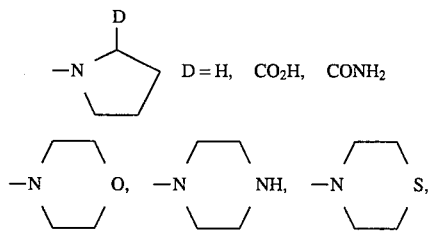

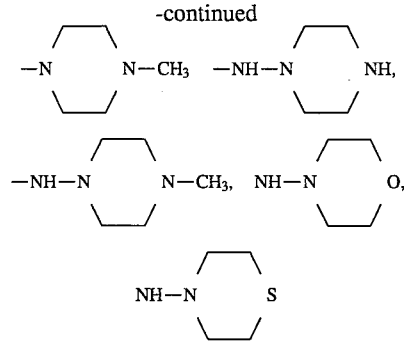

It will be appreciated that Formula I encompasses all diastereomeric entities II-VIII.

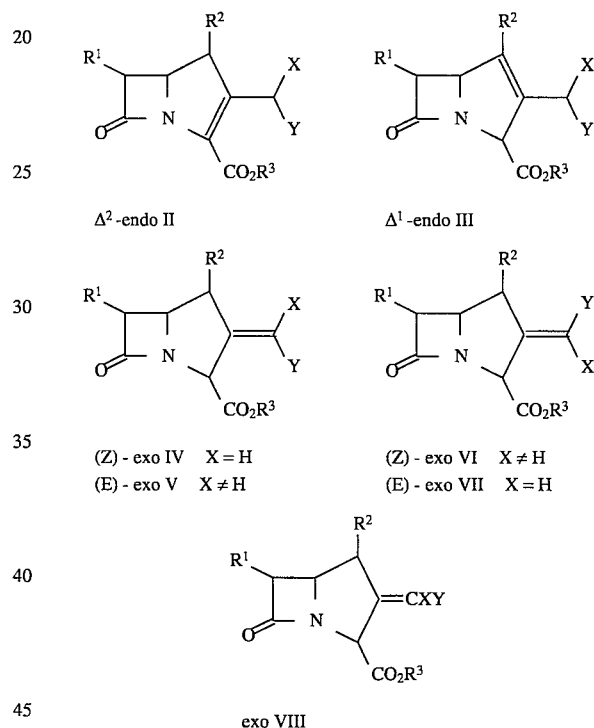

(Z) - exo IV   X = H
(E) - exo V    X ≠ H (Z) - exo VI   X ≠ H
(E) - exo VII  X = H exo VIII The exo isomers can exist as E and Z forms and this is dependent on the nature of X. If X=H then Formulas V and VII represent the E isomer for all values of Y. On the other hand, if X=F, Cl, Br, or I, then Formulas IV and VI represent z-isomeric forms provided Y does not also represent a halogen. Also, Formula VIII represents mixtures of E- and Z-isomers.

Removal of the ester blocking group of I results in a compound of the structural Formula IX:

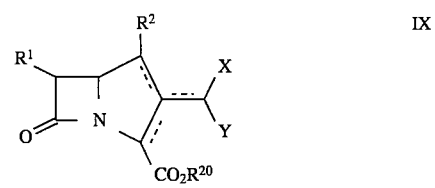

IX wherein $R^{20}$ is H or a water soluble cation such as, but not limited to, lithium, sodium and potassium or a physiologically active ester group such as pivaloyl methoxy methyl and IX encompasses the $\Delta^1$- and $\Delta^2$- endo as well as the exo forms X–XVI shown below.

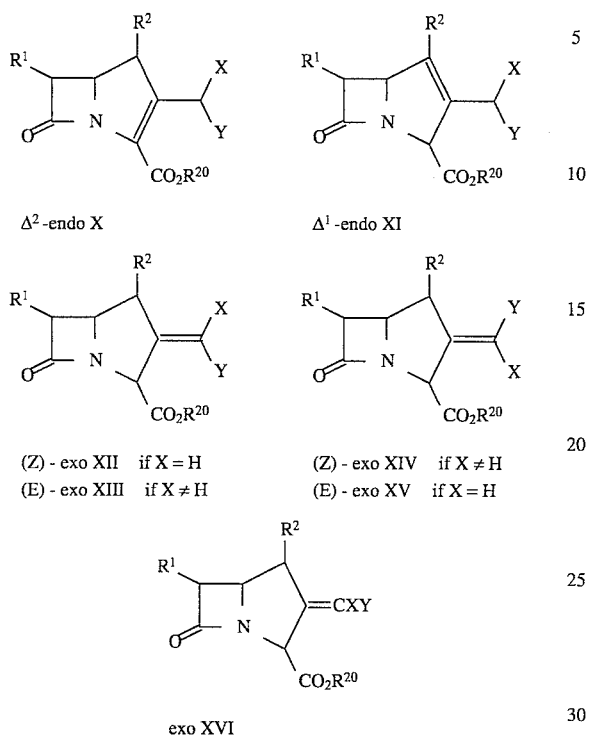

(Z) - exo XII if X = H
(E) - exo XIII if X ≠ H (Z) - exo XIV if X ≠ H
(E) - exo XV if X = H exo XVI The novel carbapenems of the present invention are produced by treating a tri- or tetra-substituted allylazetidinone of Formula XVII in an inert solvent with an appropriate base such as lithium bis(trimethylsilyl)amide under an inert atmosphere using a temperature range of –90° C. to 20° C. with –80° being the optimum temperature.

The tri- or tetra-substituted allylazetidinones which are used to make the carbapenems of the present invention have the formula:

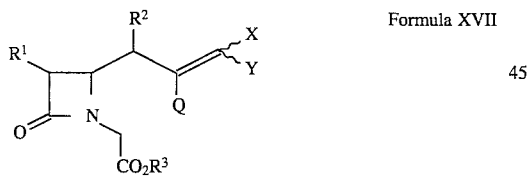

Formula XVII wherein $R^1$ is a hydrogen; a straight-chain or branched lower alkyl group such as methyl, ethyl, n-propyl, isopropyl, n-butyl, isobutyl, sec-butyl, tert-butyl, n-pentyl, or isopentyl; a straight-chained or branched lower alkoxy group such as methoxy, ethoxy, n-propoxy, isopropoxy, n-butoxy, isobutoxy, sec-butoxy, or tert-butoxy; or a $R^4$ B group [wherein $R^4$ is a hydroxyl group; a lower or isopropoxy; alkoxy group such as methoxy, ethoxy, n-propoxy, fluoride; an acyloxy group such as a lower aliphatic acyloxy group (e.g., acetoxy, propionyloxy, n-butyryloxy, or isobutyryloxy) or an aralkyloxycarbonyloxy group (e.g., benzyloxycarbonyloxy or p-nitrobenzyloxycarbonyloxy); a lower alkylsulfonyloxy group such as methanesulfonyloxy, ethanesulfonyloxy, or propanesulfonyloxy; an arylsulfonyloxy group such as benzenesulfonyloxy or p-toluenesulfonyloxy; a lower trialkylsilyloxy group such as trimethylsilyloxy or tert-butyldimethylsilyloxy; a mercapto group; a lower alkylthio group such as methylthio, ethylthio, n-propylthio, or isopropylthio; an amino group; or a lower aliphatic acylamino group such as acetylamino, propionylamino, n-butyrylamino, or isobutyrylamino; and B is-an alkylene group that may have trifluoromethyl or phenyl substituents, such as methylene, ethylene, ethylidene, trimethylene, propylidene, isopropylidene, tetramethylene, butylidene, pentamethylene, pentylidene, 2,2,2-trifluoroethylidene, 3,3,3-trifluoropropylidene, or benzylidene;

$R^2$=H, or substituted by substituent groups previously disclosed for other carbapenem derivatives. More specifically, $R^2$ may be hydrogen or any of the non-hydrogen 1-substituents disclosed for example, in European Patent Application No. 54,917 (see definition of $R^1$ or $R^2$ therein) or in U.S. Pat. No. 4,350,631. Preferred non-hydrogen $R^2$ substituents include $(C_1-C_6)$ alkyl, most preferably, methyl, phenyl and phenyl $(C_1-C_6)$ alkyl. The non-hydrogen $R^2$ substituent may be in either α-or β-configuration, and it is intended that the present invention include the individual α-and β-isomers, as well as mixtures thereof. The most preferred 1-substituted compounds are those having the β-configuration, especially those having the β-methyl substituent;

$R^3$ is a hydrogen atom; a straight-chain or branched lower alkyl group such as methyl, ethyl, n-propyl, isopropyl, n-butyl, isobutyl, or tert-butyl; a lower haloalkyl group such as 2-iodoethyl, 2,2-dibromoethyl, or 2,2,2-trichloroethyl; a lower alkoxymethyl group such as methoxymethyl, ethoxymethyl, n-propoxymethyl, isopropoxymethyl, n-butoxymethyl, or isobutoxymethyl; a lower aliphatic acyloxymethyl group such as acetoxymethyl, propionyloxymethyl, n-butyryloxymethyl, isobutyryloxymethyl, or pivaloyloxymethyl; a 1-(lower alkoxy)carbonyloxyethyl group such as 1-methoxycarbonyloxyethyl, 1-ethoxycarbonyloxyethyl, 1-n-propoxycarbonyloxyethyl, 1-isopropoxycarbonyloxyethyl, 1-n-butoxycarbonyloxyethyl, or 1-isobutoxycarbonyloxyethyl; an aralkyl group such,as benzyl, p-methoxybenzyl, o-nitrobenzyl, or p-nitrobenzyl; a benzhydryl group; a phthalidyl group a silyl such as trimethylsilyl or t-butyldimethylsilyl or 2-trimethylsilylethyl; an allylic group such as allyl, 2-chloro-2-propenyl, 2-butenyl, 3-methyl-2-butenyl or 2-cinnamyl or water soluble cations such as lithium, sodium, potassium, ammonium or tetraalkyl ammonium (alkyl of $C_1-C_4$);

Q=any suitable leaving group as defined in greater detail herein;

X=fluorine chlorine, bromine, iodine hydrogen;

Y=any suitable electron withdrawing group as defined in greater detail herein.

In Formula XVII, Y can be any suitable electron withdrawing group such as, but not limited to, $CO_2H$, $CO_2R^{16}$,

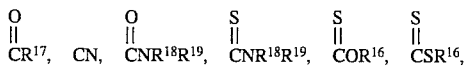

$SO_2R^{17}$, $SOR^{17}$, $SR^{17}$, F, Cl, Br, I.

In Formula XVII, Q can be any suitable leaving group commonly used in this type of reaction. Some representative examples are: F, Cl, Br, I, $R^{21}S$, $R^{21}SO_2$, $NR^{21}_3$, $PR^{21}_3$, $OCOR^{21}$, OOH, $OOR^{21}$, —OP(O) $(OPh)_2$, —OP(O)

(OCCl$_3$)$_2$, —OSO$_2$Ph, —OSO$_2$(4-nitrophenyl), —OSO$_2$CH$_3$ and CN. R$^{21}$=alkyl groups which may be straight or branched chain having 1–10 carbon atoms; preferred are 1–6, most preferably are 1–4 carbon groups such as methyl ethyl, n-propyl, iso-propyl, n-butyl; phenyl-substituted alkyl group such as benzyl, benzhydryl CH(C$_6$H$_6$)$_2$, 2-phenylethyl; phenyl, optionally substituted by 1–3 substituents independently selected from fluoro, chloro, bromo, C$_1$–C$_3$ alkyl, SO$_2$R$^{17}$, CO$_2$R$^{16}$, CONR$^{18}$R$^{19}$, wherein R$^{16}$–R$^{19}$ are defined hereinabove.

DESCRIPTION OF THE PREFERRED EMBODIMENTS

Novel carbapenems according to the present invention are produced according to the following reaction schemes:

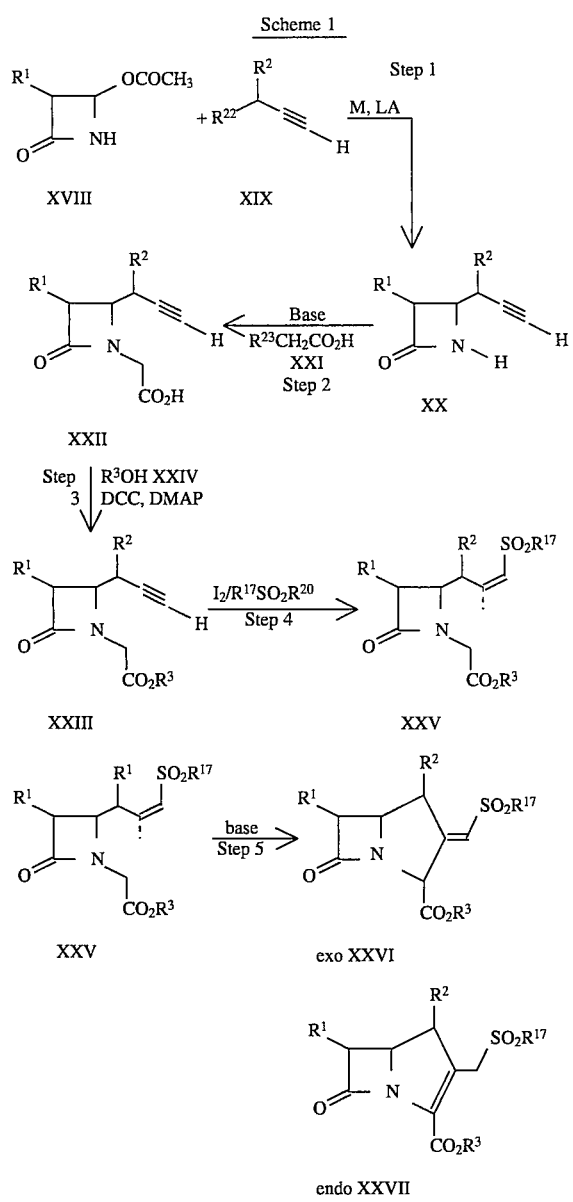

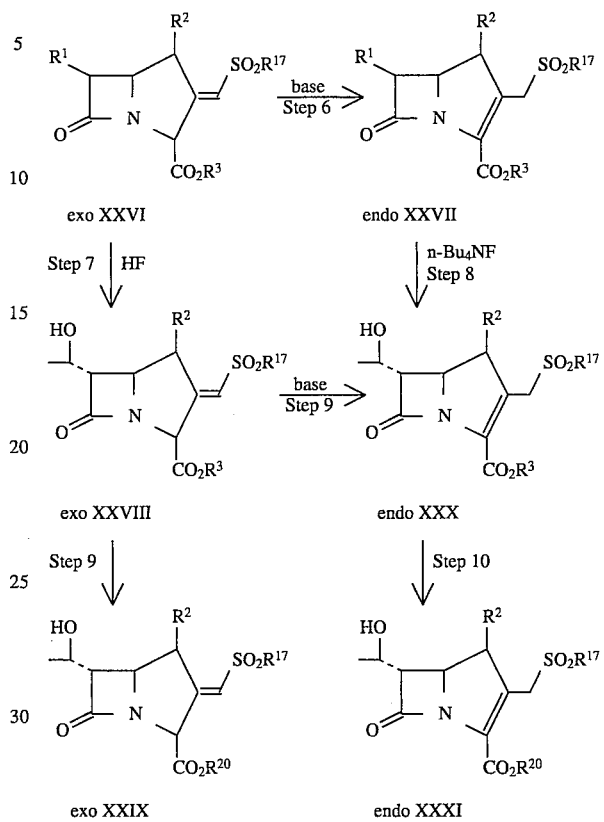

In Step 1 of Scheme 1, the propargyl azetidinone compound of Formula XX is formed on contacting the acetoxyazetidinone XVIII and the propargyl halide XIX with an elemental metal M in the presence of a Lewis acid LA wherein R$^1$ and R$^2$ are as defined hereinbefore, and R$^{22}$ is Cl, Br or I, M is Zn or Mg with Zn being preferred, LA is a suitable Lewis acid, such as, but not limited to, diethylaluminum chloride; in the presence of a suitable solvent such as tetrahydrofuran, toluene, diethyl ether or dimethoxyethane with tetrahydrofuran preferred. An excess of reagents XIX, M and LA are preferred relative to XVIII generally in the ratio of 1.5:1.5:1.5:1, respectively. Reaction concentrations usually are maintained in the range of 0.2 to 0.5 molar for the limiting reagent (XVIII).

The acetoxyazetidinone XVIII and propargyl halide XIX can be contacted with the Metal M and Lewis acid LA at temperatures ranging from about zero degrees centigrade (0° C.) to about ambient (25° C.). The inclusion of the Lewis acid LA is not mandatory for the formation of XX, however, optimum yields of XX are obtained when Step 1 is performed in the presence of Lewis acid. Contact times usually are on the order 2–12 hours and preferably 2–5 hours. The reaction product XX is isolated after a sequence which initially involves the addition of a 2.5 molar excess of a weak aromatic base such as pyridine over a 1 hour period followed by conventional techniques in the art including filtration, washing, crystallization, chromatography and the like. Yields of product XX are in the range of 30 to 90% and preferably 70%.

In Step 2 of Scheme 1, the nitrogen of the propargyl azetidinone XX is alkylated with a functionalized acetic acid of Formula XXI. The product XXII is formed on contacting XX and XXI with a suitable base such as, but not limited to, lithium bis(trimethylsilyl)amide, lithium hydride or sodium hydride in an appropriate mixed solvent system such as diethyl ether: N,N-dimethylformamide (DMF), toluene: DMF or tetrahydrofuran: DMF, preferably tetrahydrofuran: DMF. In reagent XXI, $R^{23}$ can be, but is not limited to, chloro, bromo, iodo, toluenesulfonyl, but preferably bromo.

An excess of reagents XXI and the base relative to XX generally is preferred in the ratio of 1.2:3.2:1, respectively. Reaction concentrations usually are maintained in the range of 0.2 to 0.5 molar for the limiting reagent XX. Compound XX and XXI can be contacted with the base at temperatures ranging from 0° C. to ambient under an inert atmosphere (ambient pressure) of nitrogen or argon over a period of 2–18 hours, preferably 12 hours.

The reaction product XXII is isolated by conventional techniques in the art including dilute mineral acid wash, filtration, aqueous washing, crystallization. Yields of XXII are in the range of 30 to 80% and preferably 60–70%.

In Step 3 of Scheme 1, acid XXII is esterified to the ester XXIII by contacting XXII with an alcohol XXIV, dicyclohexylcarbodiimide (DCC) and 4-dimethylaminopyridine (DMAP) according to the generalized procedure of A. Hassner Tetrahedron Lett., (1978) pg. 4475, wherein $R^3$ is defined above. Yields of product XXIII are in the range of 30–95% and preferably 80–90%.

In Step 4 of Scheme 1, the terminal acetylene XXIII is regioselectively and stereospecifically converted to the iodovinyl sulfone XXV wherein $R^{17}$ and $R^{20}$ are defined above. The reaction procedure to prepare compound of Formula XXV follows that described in W. Truce et. al. *J. Org. Chem.* (1971) Vol. 36, no. 3, pp. 1727–31 and also that of T. Kobayashi et. al. *Chem. Lett.* (1987) pp. 1209–1212. Yields of product XXV are in the range of 20 to 88% and preferably 70–80%.

In Step 5 of Scheme 1, compounds of the Formula XXV are contacted with an appropriate base in a suitable solvent at temperatures of –100° C. to ambient. While any suitable temperature may be employed it is preferred to use temperatures of –100° to –70° to eliminate undesired decomposition. The resulting Michael addition-elimination reaction produces carbapenems XXVI and XXVII.

Suitable bases that can be employed in Step 5 generally are non-aqueous ones and comprise the following:

lithium diisopropylamide
lithium bis(trimethylsilyl)amide
sodium bis(trimethylsilyl)amide
potassium bis(trimethylsilyl)amide
potassium t-butoxide
diethylamino magnesium bromide
diisopropylamino magnesium bromide
lithium diethylamide
Grignard reagents such as other alkyl (primary, secondary and tertiary) magnesium halides
lithium N-methyl anilide
methyl anilino magnesium bromide
lithium, sodium or potassium piperidide
lithium, sodium or potassium naphthalenide
lithium, sodium or potassium isopropoxide
alkalai salts of dimethyl sulfoxide
1,8-diazabicyclo[5.4.0]undec-7-ene (DBU)
1,5-diazabicyclo[4.3.0]non-5-ene (DBN)
alkyl lithiums such as primary, secondary or tertiary lithiums for instance; n-butyl lithium, sec-butyl lithium and tert-butyllithium
lithium, sodium of potassium hydride Other strong bases which may be suitably employed are disclosed in "Modern Synthetic Reactions" by H. House, W. A. Benjamin, Inc., Menlo Park, Calif., 1972.

Suitable solvents that can be employed are generally anhydrous aprotic solvents such as, but not limited to:

tetrahydrofuran (THF)
diethyl ether
dimethoxyethane (DME)
dimethylformamide (DMF)
N,N-dimethylacetamide (DMA)
N,N-dimethyl pyrrolidinone (DMP)
1,4-dioxane
acetonitrile
ethylacetate
hexanes, pentane, heptane, cyclohexane The solvent can be employed in amounts effective to solubilize the allylazetidinone XXV. Generally, solutions of XXV in the range of 0.05 to 2.0 molar are used in the Michael addition-elimination cyclization reaction preferably a concentration of 0.15 to 0.5 molar is used.

The allylazetidinone in Step 5 of Scheme 1 can be contacted with a range of 1.1 to 3 equivalents of a suitable base preferably 1.3 equivalents of lithium bis(trimethylsilyl)amide at a suitable temperature for time periods ranging from 0.1 to 3.0 hours, preferably 0.75 hours under an inert atmosphere of argon or nitrogen.

The reaction products XXVI and XXVII are isolated after a sequence of adding 2–5 equivalents of a weak acid whose acidity lies in the range of pH=4–5 such as acetic acid or an aqueous solution of potassium dihydrogen phosphate followed by temperature equilibration to 0° C. and then by conventional techniques in the art including washing, crystallization or chromatography. Combined yields of products XXVI and XXVII are in the range of 10 to 70%.

Also a subject of this invention is a method for converting the exo-carbapenem XXVI to the endo-isomer XXVII. Contacting the exo-isomer XXVI with a suitable tertiary amine base in a suitable solvent in a temperature range of 0° to 40° C. gives the endo-isomer XXVII over a time range of 1 to 24 hours.

Suitable amines include triethylamine, diisobutylethylamine, 1,8-diazabicyclo[5.4.0]undec-7-ene with diisopropylethylamine preferable.

Suitable solvents include those disclosed above for cyclization of XXV with methylene chloride being preferred. The substrate XXVI is usually contacted with a 2–4 molar excess of amine in enough solvent to bring its concentration to 0.1–1.0 molar with 0.3 molar optimal. Product isolation follows conventional techniques in the art including washing with an aqueous acid solution such as potassium dihydrogen phosphate, chromatography and the like. Yields of product XXVII are in the range of 70–95%.

In the Formulae XXVI and XXVII, $R^1$ is independently selected from the list shown above. Preferred is where $R^1$ is 1-(t-butyldimethyl)siloxyethyl, 1-(trimethyl)siloxyethyl, 1-(allyloxycarbonyloxy)ethyl or 1-(benzyloxycarbonyloxy)ethyl. Removal of these types of protecting groups may be achieved by any number of conventional procedures such as acid hydrolysis for the silyl based groups and catalytic reduction for the other two which are members of the carbonate-based protective groups.

In Step 7 of Scheme 1, the preferred 1-(t-butyldimethyl)siloxyethyl group of exo-carbapenem XXVI is hydrolyzed to the 1-hydroxyethyl exo-carbapenem XXVIII via a standard procedure in the art that entails contacting XXVI with hydrogen fluoride in acetonitrile solvent according to the general procedure of R. F. Newton et. al. *Tetrahedron Lett.,* (1979) no. 41, pp. 3981–3982. Product yields for this step range from 40–80% with 60–70% being preferred.

Similarly, the preferred 1-(t-butyldimethyl)siloxyethyl group of the endo-carbapenem XXVII is hydrolyzed in Step 8 of Scheme 1 to the 1-hydroxyethyl endo-carbapenem XXX via a tetra-n-butylammonium fluoride hydrolytic procedure standard for the art according to Guthikonda et. al., *J. Med. Chem.* (1987) Vol. 30, pp. 871–880. Yields of product in this procedure range from 25–55%. It is appreciated that only the latter hydrolytic procedure (tetra-n-butylammonium fluoride) produces endo-XXX from endo XXVII. If the hydrogen fluoride method were to be employed for Step 8, it would produce only decomposition products. The tetra-n-butylammonium fluoride procedure is satisfactory for Step 7 as well as Step 8 but not as optimal for Step 7 as is the hydrogen fluoride method.

In Step 9 of Scheme 1, endo-XXX is formed from exo-XXVIII by contacting the exo-carbapenem with a tertiary amine. The method and isolated yields of product XXX are very similar with little variation from Step 6 of Scheme 1 earlier described.

Following formation of the desired carbapenems of general formula exo-XXVIII and endo-XXX, the carboxyl protecting group $R^3$ of these intermediates may be optionally removed by conventional procedures such as solvolysis, chemical reduction or hydrogenation. Where a protecting group such as p-nitrobenzyl, benzyl or benzhydryl is used which can be removed by catalytic hydrogenation, intermediates XXVIII or XXX in a suitable solvent such as dioxane-water-ethanol, tetrahydrofuran-diethylether-buffer, tetrahydrofuran-aqueous dipotassium hydrogen phosphate-isopropanol or the like may be treated under a hydrogen pressure of from 1 to 4 atmospheres in the presence of a hydrogenation catalyst such as palladium on charcoal, palladium hydroxide, platinum oxide or the like at a temperature from 0° to 40° C. or from about 0.2 to 4 hours. Protecting groups such as 2,2,2-trichloroethyl may be removed by mild zinc reduction. The allyl protecting group may be removed by using a catalyst comprising a mixture of a palladium compound and triphenylphosphine in a suitable aprotic solvent such as tetrahydrofuran, methylene chloride or diethyl ether. Similarly, other conventional carboxyl protecting groups may be removed by methods known to those skilled in the art.

Finally, compounds of Formulae exo-XXVIII and endo-XXX where $R^3$ is a physiologically hydrolyzable ester such as acetoxymethyl, pivaloyloxymethyl, methoxymethyl, etc., may be administered directly to the host without deblocking since such esters are hydrolyzed in vivo under physiological conditions.

Thus, carbapenems exo-XXIX and endo-XXXI can be separately prepared according to Steps 9 and 10 of Scheme 1 respectively, wherein $R^{20}$ is defined as above. Depending on the carboxyl protecting group, the method of deprotection, as described above, will vary. Product isolation from the deprotection step again varies based on the method used but all methods used in this transformation follows conventional techniques in the art including chromatography and lyophilization. Product yields of exo-XXIX or endo-XXXI vary in the range of 10–80% with 50–60% preferable.

A variation of Scheme 1 allows the preparation of other carbapenems according to the present invention and these preparations follow in Scheme 2.

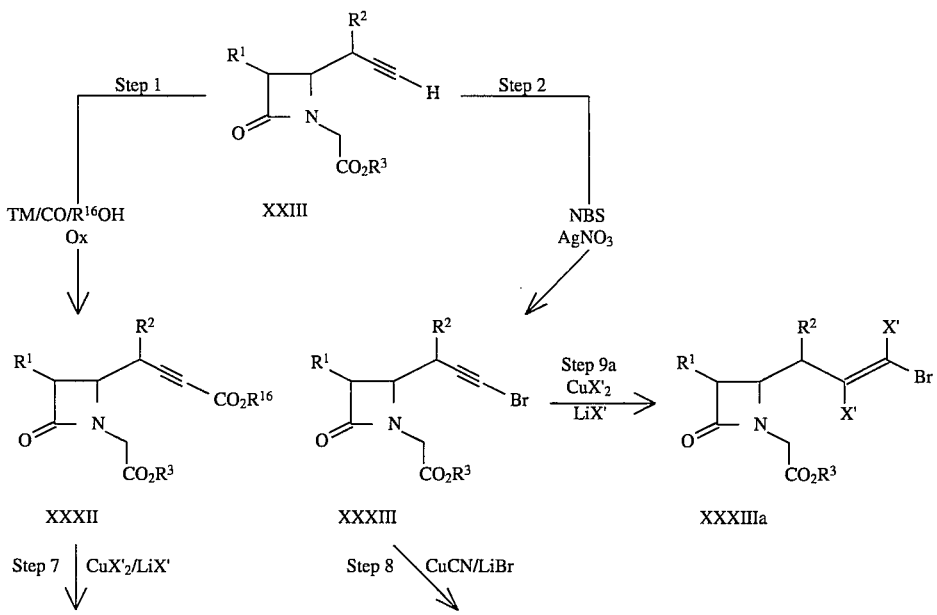

Scheme 2

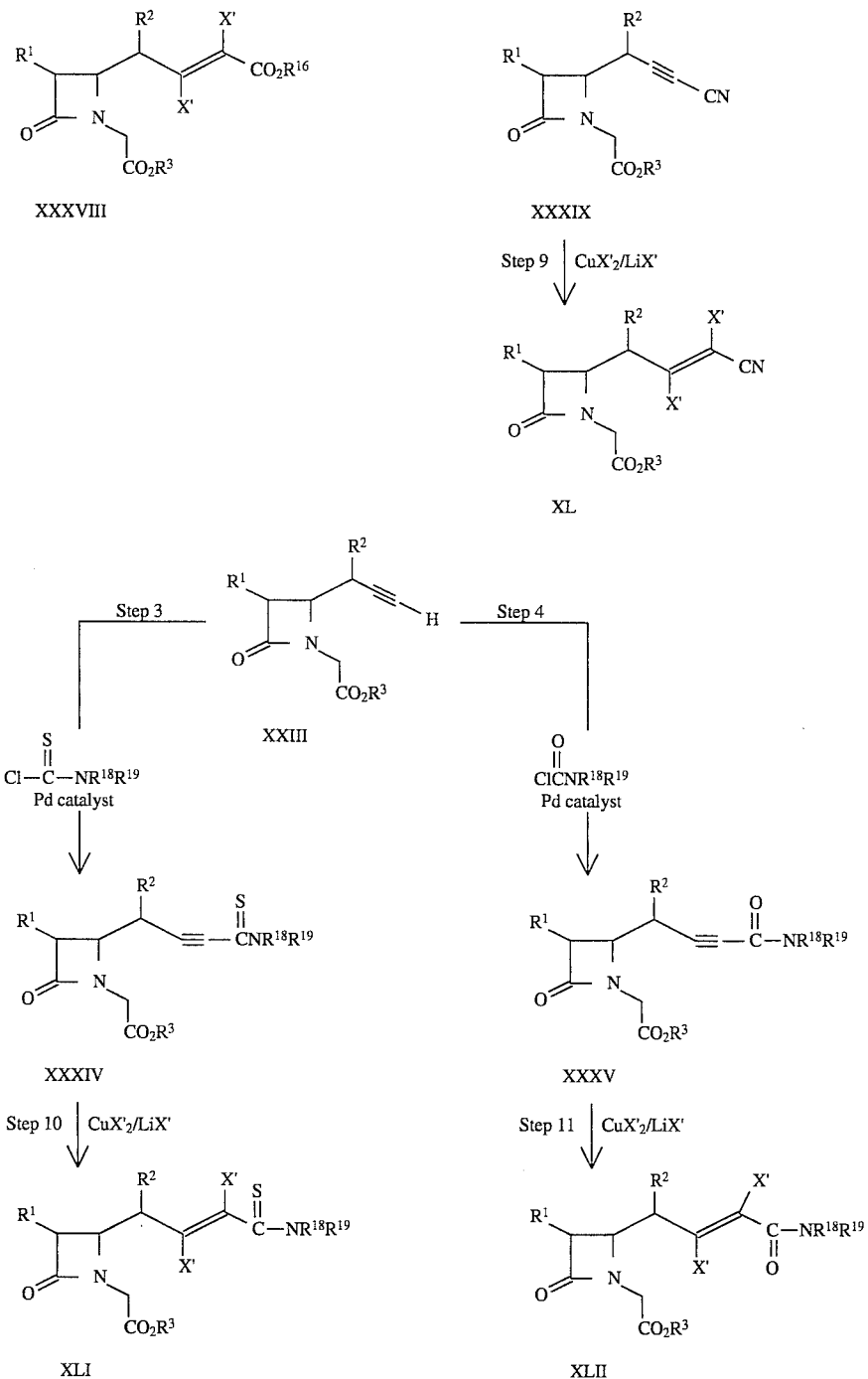

-continued
Scheme 2

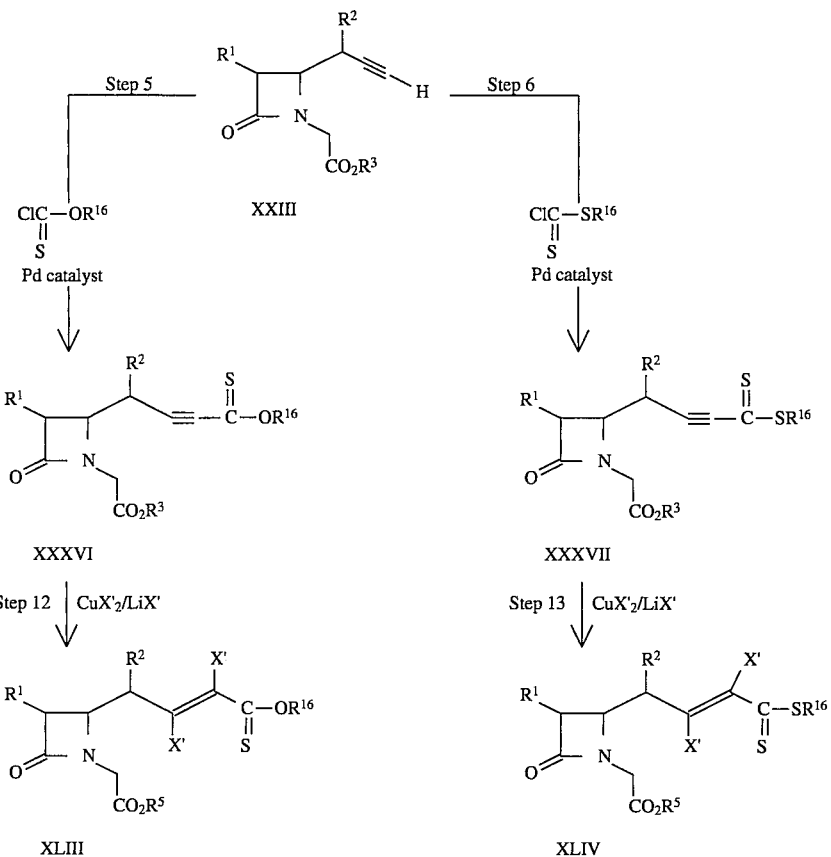

In Step 1 of Scheme 2, the propargyl azetidinone ester XXIII, whose synthesis having been discussed above as relevant to Scheme 1, is converted to the acetylenic ester XXXII, wherein $R^1$, $R^2$, $R^3$ and $R^{16}$ are defined hereinabove. The acetylenic ester XXXII is formed on contacting the terminal acetylene XXIII with a transition metal catalyst TM such as palladium dichloride, palladium diacetate, palladium bis(trifluoroacetate) or nickel dichloride with palladium dichloride being preferred. Amounts of this catalyst used in Step 1 vary from 1 mole percent to 10 mole percent based on the terminal acetylene XXIII. An oxidant Ox is employed to drive the catalytic cycle. Typical oxidants are anhydrous copper salts such as copper (II) acetate, copper (II) chloride, etc. with copper II chloride being preferred. The oxidant is usually added in amounts of 1.5 to 3.5 equivalents based on XXIII with 2.0 equivalents favored. Step 1 of Scheme 2 is conducted in an alcohol solvent, $R^{16}OH$, which also serves as a reactant. Substrate concentrations range from 0.05 to 5 molar with 0.1 to 1 molar preferred. If the alcohol $R^{16}OH$ is a solid, an inert co-solvent can be used while maintaining the desired concentrations. Suitable co-solvents are tetrahydrofuran, acetonitrile, diethyl ether, etc. The reaction is carried out in the presence of a suitable buffer such as sodium acetate in the range of 1.5 to 3.5 equivalents based on starting acetylene. The reaction is best carried out in a carbon monoxide saturated solution and under 1 atmosphere of carbon monoxide. Higher pressures of carbon monoxide may be used but to no real advantage. Reaction times vary from 0.5 to 10 hours with 1–3 hours being typical. Product isolation follows conventional techniques in the art including washing, filtering, crystallization or chromatography. Product yields vary on $R^{16}OH$ and are in the range of 20 to 85% with 50–70% being preferable. This procedure has been performed on non-related, terminal acetylenes according to J. Tsuji et. al., *Tetrahedron Lett.* (1980) Vol. 21, pp. 849–51. Other methods for converting a terminal acetylene to an acetylenic ester are common in the art. The above described method is preferred.

In Step 2 of Scheme 2, the 1-bromoacetylenic azetidinone XXXIII is formed by contacting the terminal azetidinone XXIII with a suitable brominating reagent. Several methods exist in the art for converting a terminal acetylene to a 1-bromoacetylene and many of which are detailed in L. Brandsma "Preparative Acetylenic Chemistry" 2nd edition, Elsevier 1988, Chapter VIII. The preferred method involves contacting terminal acetylene XXIII with n-bromosuccinimide (NBS) in the presence of a silver salt catalyst such as silver nitrate in a suitable aprotic solvent such as acetone. The method is similar to that reported in H. Hofmeister et. al., *Ang. Chem. Int. Ed. Engl.* (1984) Vol. 23, pp. 727–8.

In Step 3 of Scheme 2, the propargylic azetidinone ester XXIII is converted to an acetylenic thioamide XXXIV by contacting XXIII with a suitable thiocarbamoyl chloride, wherein $R^{18}$ and $R^{19}$ are defined above, in the presence of a suitable catalyst, such as bis-(triphenylphosphine)palladium dichloride, and copper (I) salt co-catalyst salt such as copper (I) iodide in a solvent such as acetonitrile. Such an overall transformation in Step 3 is common in the art and the procedure described in K. Hartke, et. al., *Tetrahedron Lett.* (1989) Vol. 30, no. 9, pp. 1073–1076 provides the preferred procedure.

Product isolation in Step 3 of Scheme 2 follows conventional techniques in the art including washing, filtering, crystallization or chromatography. Product yields range from 40–85%.

By similar techniques that are performed in Step 3, it will be appreciated that by the substitution of a suitable carbamoyl chloride of formula Cl—CONR$^{18}$, R$^{19}$ acetylenic amides can be obtained via this procedure. Thus, Step 4 of Scheme 2 shows the conversion of terminal acetylene XXIII to the corresponding acetylenic amide XXXV. Similar product yields as XXXIV are realized for XXXV. The methodology of Scheme 2 described in Steps 3 and 4 can be further extended to the preparation of thionoester XXXVI, from the terminal acetylenic azetidinone XXIII shown in Step 5, Scheme 2. Dithioesters XXXVII, similarly, can be prepared in Step 6. In both Steps 5 and 6, acetylene XXIII, when contacted with thiocarbonyl chlorides of formula Cl—C(S)OR$^{16}$ or dithiocarbonyl chlorides of formula Cl—C(S)SR$^{16}$ under the catalytic reaction conditions of Step 3 yields esters XXXVI and XXXVII respectively. Yields vary from 10 to 75% for these products.

In Step 7 of Scheme 2, the acetylenic diester XXXII is converted to the dihaloester XXXVIII by contacting XXXII with a suitable halogenating reagent, wherein X' is defined as chloride, bromine and iodine. The art offers several methods of acetylene halogenation, many of which are useful for the transformation of Step 7 and these are found in S. Patai (ed.) "The Chemistry of the Carbon-Carbon Triple Bond" Part 1, J. Wiley, 1978, pp. 320–327. The preferred method for Step 7 entails contacting the acetylene XXXII with an anhydrous copper (II) halide and lithium halide such as copper (II) chloride, lithium chloride pair or copper (II) bromide, lithium bromide pair in a suitable solvent such as acetonitrile under an inert atmosphere such as argon in a temperature range of 25° to 100° C. preferably 80° C. for a period of time ranging from 1–16 hours, usually 6–8 hours are preferred. The method described above is the same reported for the halogenation of unrelated acetylenes as described by S. Uemura et. al. *J. Chem. Soc. Chem. Commun.* (1975) pp. 925–6. Product isolation utilizes conventional techniques in the art including filtration, washing and chromatography. Yields of product range from 50–90%.

In Step 8 of Scheme 2, the cyanoacetylene XXXIX is formed by contacting the bromoacetylene XXXIII with copper (I) cyanide and lithium bromide in a suitable solvent such as acetonitrile, diethyl ether or tetrahydrofuran whereas tetrahydrofuran is preferred. The art offers several examples of 1-bromoacetylenes forming acetylenic nitriles. Examples of such methods that would also be amenable to the conversion in Step 8 are listed in L. Brandsma in "Preparative Acetylenic Chemistry" Elseiver, 1988, Chapter 8. The preferred method and product isolation described above is found in this reference, pp. 229–230. Product yields vary from 45–85%.

In Step 9, Scheme 2, the cyanoacetylene XXXIX is converted to XL by contacting XXXIX with the above mentioned reagents and conditions described in detail for Step 7, Scheme 2. Yields of the product dihalonitrile XL vary from 55 to 90%.

In fact, the transformations described in detail for Steps 7 and 9 of Scheme 2 can be repeated in 10, 11, 12 and 13 of Scheme 2 as the overall intended in each case is to produce a osubstitution pattern from an acetylenic material. The described halogenation proce general for those acetylenic compounds sing Scheme 2. Thus, the dihalo products IV are isolated via conventional techniques in the art and their yields vary from 20 to 85%.

The preparation of other 2-alkyl-substituted-3-carboxy-carbapenems relies on a variation of the general synthesis of Schemes 1 and 2. In Scheme 3, a synthetic route that utilizes the propargyl azetidinone XXII, prepared as shown in Scheme 1, as the starting point for the synthesis of carbapenems of general Formula I wherein Y is COR$^{17}$.

In Step 1 of Scheme 3, the propargyl alcohol XLV is formed from XXII via a sequential treatment of XXII with two equivalents of a suitable strong base such as n-butyllithium in a suitable solvent such as tetrahydrofuran under an inert atmosphere such as argon at a temperature range of −80 to 0° C. preferably −70° C. Generally, the amount of solvent used is enough to effect solubilization of the acid XXII with an ultimate concentration range of 0.05 to 2 molar acceptable, preferably 0.1 to 0.3 molar concentration. Following the strong base treatment, a suitable aldehyde R$^{17}$CHO is contacted with the previously base treated XXII, wherein R$^{17}$ is defined as above. The amount of the aldehyde varies from about 1 to 5 equivalents based on XXII with 1.2–3 equivalents being preferred. Contact times of aldehyde with base treated XXII vary between 0.5 to 5 hours preferably 2–3 hours while the reaction temperature is allowed to vary between −80° to 20° C. with a variance of −80° to 0° C. being preferable. The reaction is completed by the addition of about 2 to 10 equivalents of a suitable weak acid, preferably 2–5 equivalents of acetic acid, to the reaction. Product isolation utilizes techniques common to the art including washing and chromatography. Yields of product XLV vary in the range 20 to 85% depending on the nature of aldehyde used with a range of 50–85% preferable.

In Step 2 of Scheme 3, the acid XLV is esterified to XLVI by any number of known procedures common to the art. Preferably the general procedure described in Scheme 1—Step 3 is employed here wherein R$^3$ is defined above.

In Step 3 of Scheme 3, the secondary alcohol XLVI is oxidized to the corresponding ketone XLVII. Oxidation of propargyl alcohols to propargyl ketones is common to the art with a vast number of methods available. Many of these methods are acceptable for the transformation in Step 3 such as pyridinium chlorochromate in methylene chloride, barium permanganate in methylene chloride and manganese dioxide in chloroform. Preferable in Step 3 is pyridinium chlorochromate (PCC) in methylene chloride. A methylene chloride solution containing XLVI at a concentration of about 0.05 to 3 molar, preferably 0.2 molar to 1 molar is contacted with about 1.2 to 5 molar equivalents of PCC, preferably 2 to 3 equivalents at a temperature range of about 0° to ambient, preferably ambient, over a time range of 1–24 hours, preferably 1–4 hours. Product isolation utilizes common techniques in the art including filtration, washing and chromatography. Product yields of XLVII vary from 30 to 90% with 60 to 90% being preferred.

In Step 4 of Scheme 3, the dichloro unsaturated ketone XLVIII is formed by contacting XLVII with the identical reagents and reaction conditions described in detail in Scheme 2—Steps 7, 9–13. Product yields of XLVIII range from 30 to 70%.

Scheme 3

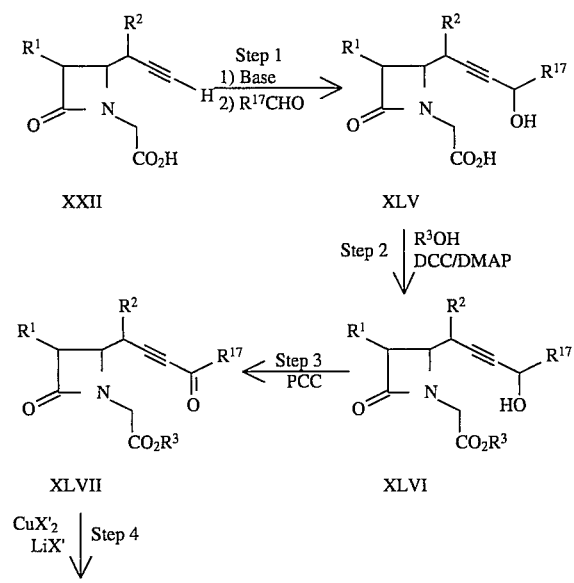

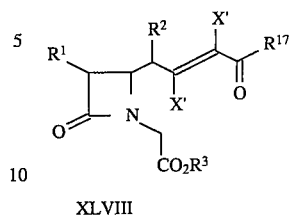

In Scheme 4—Step 1, the tetrasubstituted allylazetidinone XLIX undergoes an intermolecular Michael addition-elimination reaction With a nucleophile Q to form L wherein Q, $R^1$, $R^2$, $R^3$, X' and Y are hereinabove defined. Compound L is prepared when the dihalo compound XLIX is contacted with a suitable nucleophile Q in a suitable solvent, such as, but not limited to, acetone, acetonitrile, dimethoxyethane, dimethylformamide, methanol, ethanol, pyridine at a temperature range of about 0° to 80°, preferably 20° to 50° C. range for a time period ranging from 1–24 hours depending on the nature of X' and Q. The above described, reaction is not crucial to the subsequent reaction, which is the carbapenem forming ring closure.

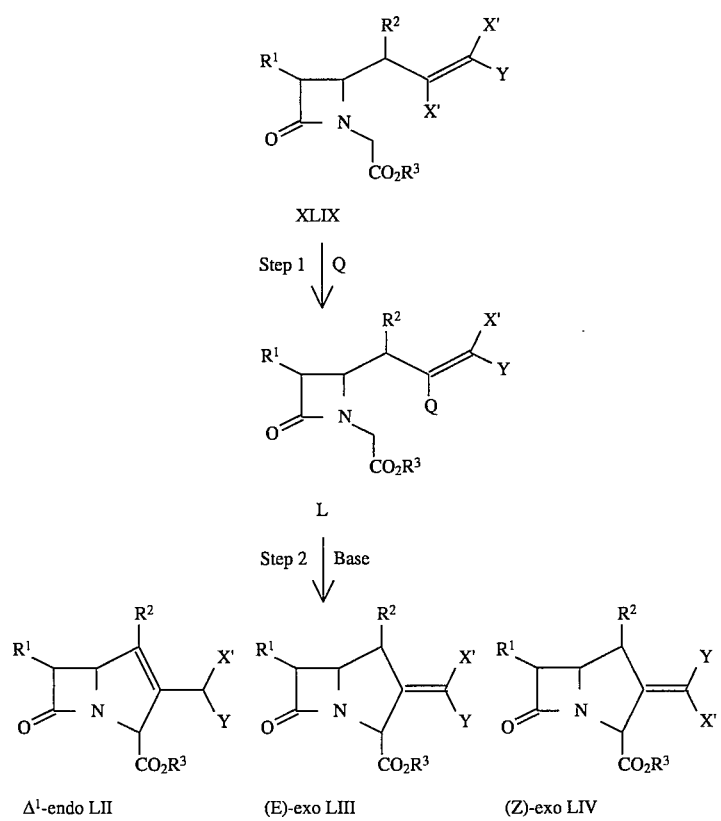

-continued
Scheme 4

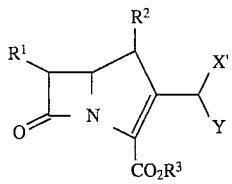

$\Delta^2$-endo LV

Step 1 in Scheme 4 is optional for purposes of replacing X' with a group Q that has better leaving group propensity over X'. It is recognized to those familiar with the art that addition-elimination reactions, key to the invention herein described, can be improved through the judicious choice of the leaving group Q. This improvement can manifest itself in such things as improved yields of carbapenems, less decomposition of Compound L and shorter or expedient reaction times This emperical observation is described in detail for simple systems in J March, "Advanced Organic Chemistry", J. Wiley, Third edition, 1985, pp. 295–296. Thus, it is the purpose of Step 1 to prepare a compound of Formula L from XLIX that possesses optimum reactivity in the Michael addition-elimination reaction that forms the 2-alkylsubstituted-3-carboxycarbapenems.

In Step 2 of Scheme 4, compound L is contacted with an appropriate base in a suitable solvent at temperatures of –100° C. to ambient. While any suitable temperature may be employed, it is preferable to use temperatures of –100° to –40° to eliminate undesired decomposition. The resulting Michael addition-elimination reaction produces carbapenems LI to LV in varying amounts. The factors that control the relative ratio of carbapenem products LII–LV in the ring closure in Step 2 include, but are not entirely confined to, structural features such as Y and X', reaction time, reaction temperature, base strength and the amount of excess base.

Suitable bases that can be employed in Step 2 generally are non-aqueous ones and are described hereinabove for Scheme 1—Step 5. Likewise, suitable solvents that can be employed are generally anhydrous, aprotic solvents and are detailed hereinabove in Scheme 1—Step 5.

The solvent can be employed in amounts effective to solubilize the compound L. Generally, solutions of L in the concentration range of 0.05 to 2.0 molar are used in Step 2 of Scheme 4. Preferably, a concentration of 0.15 to 0.5 molar.

The allylazetidinone can be contacted with a range of 1.1 to 3 equivalents of a suitable base defined above preferably 1.3 equivalents of lithium bis(trimethylsilyl)amide at a suitable temperature for time periods ranging from 0.1 to 3.0 hours, preferably 0.75 hours under an inert atmosphere of argon or nitrogen.

The reaction products LII–LV are isolated following a sequence of adding 2–5 equivalents of a weak acid whose acidity lies in the range of pH=4–5 such as acetic acid or an aqueous solution of potassium dihydrogen phosphate followed by temperature equilibration to 0° C. and then by conventional techniques in the art including washing, crystallization or chromatography. Combined yields of products LII–LV lie in the range of 10 to 70%.

Also a subject of this invention is a method for converting the $\Delta^1$-endo LII, (E)-exo LIII and (Z)-exo LIV isomers to the $\Delta^2$-endo isomer LV. This is shown in Scheme 5.

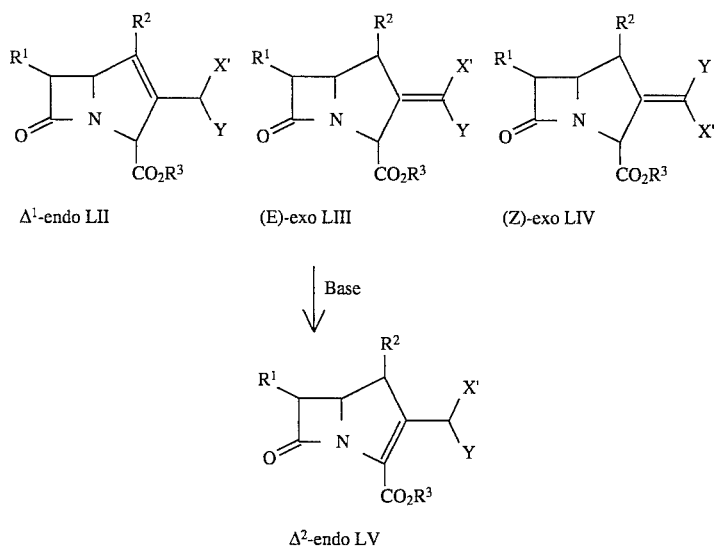

Contacting the $\Delta^1$-endo isomer LII and/or the exo isomers LIII and LIV with a suitable tertiary amine base in a suitable solvent in a temperature range of −70° to 40° C. gives the endo isomer LV over a time range of 0.25 to 24 hours with −70° to −20° C. preferred over a period of 0.25 to 0.75 hours.

Suitable amines include triethylamine, diisobutylethylamine, 1,8-diazabicyclo[5.4.0]undec-7-ene (DBU) or 1,5-diazabicyclo[4.3.0]non-5-ene (DBN) with DBU being preferred.

Suitable solvents include methylene chloride, tetrahydrofuran, acetonitrile, dimethoxyethane, acetone with methylene chloride preferred.

The $\Delta^1$-endo isomer LII and/or the exo isomers LIII and LIV are contacted with a 0.1–1.8 molar excess of amine preferably 0.9 molar excess in enough solvent to bring its concentration to 0.1–1.0 molar with 0.3 molar optimal. Product isolation follows conventional techniques in the art including washing with an aqueous acid solution such as potassium dihydrogenphosphate, chromatography and the like. Yields of product LV vary in the range of 10–95%.

In Scheme 6, the compound with Formula LVI represents exo (E) and (Z)-isomeric forms along with the endo isomer LV where $R^1$ is herein defined above. Preferred is where $R^1$ is 1-(t-butyldimethyl)siloxyethyl, 1-(trimethyl)siloxyethyl, 1-(allyloxycarbonyloxy)ethyl or 1-benzyloxycarbonyloxy-)ethyl. Removal of these types of protecting groups in Steps 1 and 2 of Scheme 6 may be achieved by any number of conventional procedures such as acid hydrolysis for the silyl based groups and catalytic reduction for the other two which are members of the carbonate-based protective groups. These commonly used deprotective procedures are well known in the art and are dealt with in the reference, T. Greene "Protective Groups in Organic Synthesis" J. Wiley, 1981, pp. 14–71.

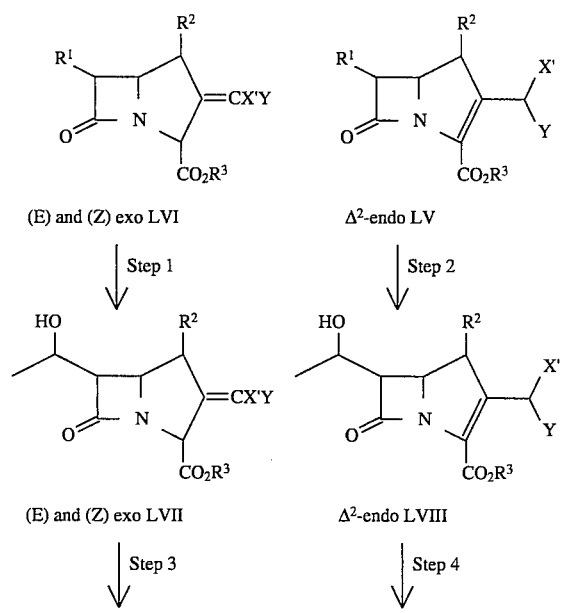

Scheme 6

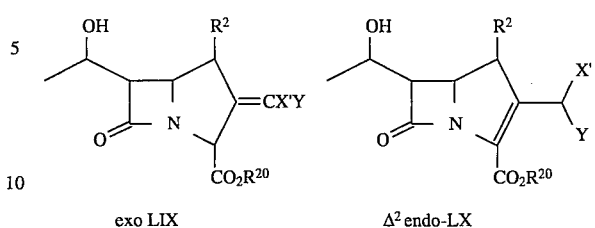

-continued
Scheme 6

Product isolation in this deprotective procedure in Steps 1 or 2 of Scheme 6 is similar and employs conventional techniques common to the art such as washing, filtering and chromatography. Product yields of exo LVII from Step 1 or endo LVIII in Step 2 vary from 20 to 85%.

Following formation of the desired carbapenems of general formula exo-LVII and endo-LVIII, the carboxyl protecting group $R^3$ of these intermediates may be optionally removed by conventional procedures such as solvolysis, chemical reduction or hydrogenation. Where a protecting group such as p-nitrobenzyl, benzyl or benzhydryl is used, it can be removed by catalytic hydrogenation. Intermediates LVII and LVIII, in a suitable solvent such as dioxane-water-ethanol, tetrahydrofuran-diethylether-buffer, tetrahydrofuran-aqueous dipotassium hydrogen phosphate-isopropanol or the like may be treated under a hydrogen pressure of from 1 to 4 atmospheres in the presence of a hydrogenation catalyst such as palladium on charcoal, palladium hydroxide, platinum oxide or the like at temperatures from 0° to 40° C. from about 0.2 to 4 hours. Protecting groups such as 2,2,2-trichloroethyl may be removed by mild zinc reduction. The allyl protecting group may be removed by using a catalyst comprising a mixture of a palladium compound and triphenylphosphine in a suitable aprotic solvent such as tetrahydrofuran, methylene chloride or diethyl ether. Similarly, other conventional carboxyl protecting groups may be removed by methods known to those skilled in the art.

Finally, compounds of Formula exo-LVII and endo-LVIII where $R^3$ is a physiologically hydrolyzable ester such as acetoxymethyl, pivaloyloxymethyl, methoxymethyl, etc., may be administered directly to the host without diblocking since such esters are hydrolyzed in vitro in the presence of added esterase or in vivo under physiological/conditions.

Thus, carbapenems exo-LIX and endo-LX can be separately prepared according to Steps 3 and 4 respectively, wherein $R^{20}$ is defined as above. Depending on the carboxyl protecting group, the method of deprotection, as described above, will vary. Product isolation from the deprotection step again varies, based on the method used, but all methods used in this transformation follow conventional techniques in the art including chromatography and lyophilization. Product yields of exo-LIX vary in the range of 20 to 70% and yields of endo-LX vary from 10 to 60%.

It will be appreciated that certain products within the scope of Formula LXI

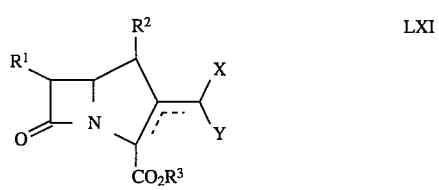

may be formed as optical isomers as well as epimeric mixtures thereof. It is intended that the present invention include within its scope all such optical isomers and epimeric mixtures. For example, when the 6-substituent in LXI is 1-(t-butyldimethyl)siloxyethyl, such substituent may be either R or S configuration with the R configuration being preferred. Likewise, the configuration of the carbapenem nucleus may be 5R or 5S and 6R or 6S with 5R, 6S being the preferred configuration.

In Vitro Activity

Samples of the carbapenem Compounds prepared in this invention after solution in water and dilution with Nutrient Broth were found to exhibit the following Minimum Inhibitory Concentrations (M.I.C.) in micrograms/ml versus the indicated microorganisms as determined by overnight incubation at 37° C. by tube dilution (Table 1).

TABLE 1

In Vitro Antibacterial Activity of Carbapenem Derivatives

| Carbapenem | Ec(1) | Ec(2) MIC | SA(1) mcg/ml | SA(2) | SM | Ent C |
|---|---|---|---|---|---|---|
| 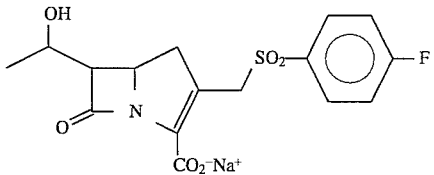 Example 48 | 8 | 8 | 0.06 | 0.06 | 32 | 64 |
| 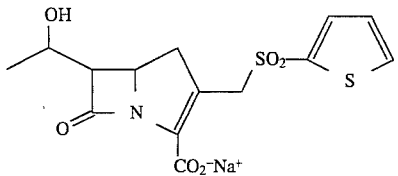 Example 10 | 1 | 1 | 0.06 | 0.06 | 32 | 32 |
| 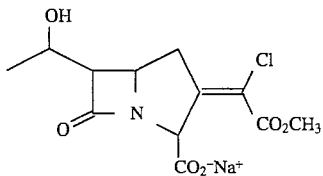 Example 44 | 128 | 128 | 64 | 64 | 128 | 128 |

Ec(1) — *E. coli* ATCC 25922;
Ec(2) — *E. coli* ATCC 35218;
SA(1) — *Staph. aureus* ATCC 29213;
SA(2) — *Staph. aureus* ACCC 25923;
SM — *Ser. marceslens;*
Ent C — *Ent. cloacae*

A sample of the carbapenems prepared in this invention is tested in combination with the penicillin Piperacillin. The enhanced combined synergistic antibacterial activity is representative of the anti β-lactamase properties of the carbapenems in this invention (Table 2).

TABLE 2

In Vitro Antibacterial Activity of Carbapenem, Piperacillin and 1:1 Combination of Carbapenem:Piperacillin a

| Organism | Example 48 M.I.C. | Piperacillin mcg/ml | + Piperacillin |
|---|---|---|---|
| E. Coli-OXA-2 | 32 | 16 | 0.5 |
| E. Coli-OXA-4 | 32 | 8 | 2 |
| E. Coli-OXA-7 | 16 | 128 | 0.5 |
| E. Coli-OXA-5 | 32 | 2 | 0.25 |
| Pseudomonas OXA-6 | 128 | 32 | 4 |

When the compounds are employed for the above utility, they may be combined with one or more pharmaceutically acceptable carriers, for example, solvents, diluents and the like, and may be administered parenterally in the form of sterile injectable solutions or suspensions containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 2 to about 100 mg/kg of animal body weight, preferably given in divided doses two to four times a day. For most large mammals, the total daily dosage is from about 100 to about 750 mg, preferably from about 100 to 500 mg. Dosage forms suitable for internal use comprise from about 100 to 750 mg of the active compound in intimate admixture with a liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered by intravenous, intramuscular, or subcutaneous routes. Liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as coloring agents, preserving agents, and antioxidants, for example, vitamin E, ascorbic acid, BHT and BHA.

These active compounds may also be administered parenterally or intraperitoneally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injection use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be more fully described in conjunction with the following specific examples which are not to be construed as limiting the scope of the invention.

EXAMPLE 1

[3S-[3Alpha(S*),4beta]]-3-[1-[[(1,1-dimethylethyl)-dimethylsilyl]oxy]ethyl]-4-(2-propynyl)-2-azetidinone To a dry three neck round bottom flask equipped with a mechanical stirrer, 1000 ml addition funnel and thermometer is added 146.6 g zinc and 1L tetrahydrofuran. The suspension is stirred at 0° under an atmosphere of argon while 800 ml diethylaluminum chloride (1.8M in toluene) is added via cannula. A solution of 320 g of [3S-[3alpha(S*),4beta]]-4-(acetyloxy)-3-[1-[[1,1-dimethylethyl)dimethylsilyl]oxy]ethyl]-2-azetidinone and 168 ml propargyl bromide (80% toluene solution) in 800 ml tetrahydrofuran is added via addition funnel over 90 minutes and the reaction mixture is stirred at 0° C. for two hours, then at room temperature overnight. The reaction mixture is cooled to 0° C. and 200 ml pyridine is added dropwise over 50 minutes. The solution is filtered through diatomaceous earth washing with dichloromethane. The filtrate is concentrated in vacuo to 1L and the solid is dissolved in dichloromethane. The resulting solution is added over 45 minutes to a stirred 3L slurry of ice/water and stirring is continued for an additional 30 minutes. The solution is filtered through hydrous magnesium silicate and the filtrate evaporated to afford 196.6 g (66.9%) after recrystallization from heptane. $^1$H NMR (CDCl$_3$) δ0,078(s,6H), 0,877(s,9H), 1.23 (d,3H), 2.05(t,H), 2.54(m,2H), 2.90(m,H), 3.86(m,H), 4.21(m,H), 5.98(brs, OH). IR (KBr) 1702, 1754 cm$^{-1}$.

EXAMPLE 2

[3S-[3Alpha(S*),4beta]]-3-[1-[[1,1-dimethylethyl)- dimethylsilyl]oxy]ethyl]-2-oxo-4-[2-propynyl-1- azetidineacetic acid A 4.48 g suspension of prewashed sodium hydride (50% dispersed in oil) in 200 ml of anhydrous tetrahydrofuran is cooled in an ice bath under argon. To this suspension is added, over a 30 minute period, a solution of 10 g azetidinone prepared in Example 1 and 6.22 g bromoacetic acid in anhydrous tetrahydrofuran. The resulting reaction mixture is stirred for an additional 20 minutes, then 16 ml dry dimethylformamide is added dropwise. The ice bath is then removed and the suspension is stirred overnight at room temperature. One hundred ml of 1N hydrochloric acid is slowly added to the suspension followed by 200 ml water. The product is extracted in 3×300 ml of ethyl acetate. The organic phase is washed with 2×200 ml of water, 2×200 ml of brine, dried over magnesium sulfate and filtered. The filtrate is evaporated to give, after recrystallization from hot hexane, 10.9 g of product (90.2%). m.p. 86°–88° C.

$^1$H NMR (CDCl$_3$) δ0.068(d,6H), 0.895(s,9H), 1.24(d, 3H), 2.07(m,H), 2.6(m,2H), 2.97(m,H), 3.98(m,H), 4.1(q, 2H), 4.2(m,H), 7.8(brs, OH).

IR (KBr) 1702, 1755 cm$^{-1}$.

EXAMPLE 3

[3S-[3Alpha(S*),4beta]]-3-[1-[[(1,1-dimethylethyl)- dimethylsilyl]oxy]ethyl]- 2-oxo-4-(2-propynyl)-1-azetidineacetic acid, 2-chloro-2-propenyl ester To a solution of 10 g of acid prepared in Example 2 in 150 ml of anhydrous tetrahydrofuran is added under argon 3.2 ml of 2-chloro-2-propen-1-ol, 0,369 g of 4-dimethylaminopyridine and 7.57 g of 1,3-dicyclohexylcarbodiimide. The resulting suspension is stirred overnight at room temperature, filtered and the filtrate evaporated to dryness. The resulting oil is dissolved in 200 ml of ethyl acetate, the cloudy solution is filtered and the filtrate washed with 100 ml portions of 5% aqueous acetic acid, water and brine. The organic phase is dried over magnesium sulfate and evaporated to dryness to give, after flash column chromatography (10–20% ethyl acetate/hexane), 6.56 g (82.2%) of the product as a colorless oil.

$^1$H NMR (CDCl$_3$) δ0.07(d,6H), 0,867(s,9H) , 1.25(d,3H) 2.05(m,H), 2.61(m,2H), 2.95(m,H), 3.96(m,H), 4.1 (q,2H), 4.71(d,2H), 5.46(d,2H).

EXAMPLE 3A

[3S-[3Alpha(S*),4beta]]-3-[1-[[(1,1-dimethylethyl)- dimethylsilyl]oxy]ethyl]- 2-oxo-3-(2-propynyl)-1-azetidineacetic acid, (4-nitrophenyl)methyl ester The title compound is prepared by the procedure of Example 3, using 11 g of Example 2, 150 ml of tetrahydrofuran, 7.04 g of 4-nitrobenzylalcohol, 0.182 g of 4-dimethylaminopyridine and 7.04 g of 1,3-dicyclohexylcarbodiimide. The reaction mixture is purified by flash chromatography to give 6.2 g (40%) of white crystalline product.

$^1$H NMR (CDCl$_3$) δ0.055(d,6H), 0.855(s,9H), 1.24(d, 3H), 1.99(m,H), 2.58(m,2H), 2.95(m,H), 3.95(m,H), 4.13 (d,2H), 4.19(m,H), 5.26(d,2H), 7.52(d,2H), 8.23(d,2H).

IR (KBr) 1193, 1350, 1526, 1735, 1761 cm$^{-1}$.

EXAMPLE 4

[2R-[2Alpha[E],3beta(R*)]]-2[3-[(2,4-difluorophenyl)- sulfonyl]- 3-iodo-2-propenyl]-3-[1-[[(1,1-dimethylethyl)dimethyl- silyl]oxy]ethyl]- 4-oxo-1-azetidineacetic acid, 2-chloro-2-propenyl ester A solution of 2 g of 2-chloro-2-propenyl ester, prepared in Example 3, 2.05 g of 2,4-difluorophenylsulfinic acid, 1.27 g of iodine, 0.965 g of sodium bicarbonate and 0.942 g of sodium acetate in 50 ml of ethyl acetate and 25 ml of water is irradiated with a 400 W bulb for 45 minutes. The resulting colorless solution is cooled to room temperature, the water phase is separated and extracted with 2×50 ml of ethyl acetate. The combined organic phase is washed with 50 ml of 5% aqueous sodium bisulfite solution, 2×50 ml of water and 50 ml of brine. The organic layer is dried over magnesium sulfate and evaporated to dryness to give, after flash column chromatography, 2.36 g (67%) of product as a colorless oil which solidifies on standing.

$^1$H NMR (CDCl$_3$) δ0.09(d,6H), 0.879(s,9H), 1.24(d,3H), 3.2(m,H), 3.39(m,2H), 3.70(m,H), 4.04(q,2H), 4.21 (m,H), 4.7(s,2H), 5.45(d,2H), 7.04(m,2H), 7.97(m,H).

EXAMPLE 4A

[2R-[2Alpha (E),3beta (R*)]]-2[3-[(3,4-dimethoxyphenyl)sulfonyl]-2-iodo-2- propenyl]-3-[1-[[(1,1-dimethylethyl)dimethylsilyl]- oxy]ethyl]-4-oxo-1-azetidineacetic acid, 2-chloro-2-propenyl ester The title compound is prepared by the procedure of Example 4, using 9.25 g of 3,4-dimethoxyphenylsulfinic acid, 6.1 g of Example 3, 3.87 g of iodine, 3.84 g of sodium bicarbonate, 3.75 g of sodium acetate, 150 ml of ethyl acetate and 75 ml of water. The reaction mixture is purified by flash chromatography to give 5.81 g (52%) of product.

$^1$H NMR (CDCl$_3$) δ0,093(d,6H), 0,881(s,9H), 1.26(d, 3H), 3.21(m,H), 3.37(m,H), 3.73(m,H), 3.96(d,6H), 3.99 (q,2H), 4.22(m,H), 4.71(s,2H), 5.46(d,2H), 7.00(d,H), 7.12(s,H), 7.31(d,H), 7.52(d,H).

CI-MS: m/z 745 (M+NH$_3$)$^+$.

EXAMPLE 4B

[2R-[2Alpha(E),3beta(R*)]]-3-[1-[[(1,1-dimethylethyl)- dimethylsilyl]oxy]ethyl]-2[3-[[4-(1,1-dimethylethyl)- phenyl]sulfonyl]- 2-iodo-2-propenyl-4-oxo-1-azetidineacetic acid, 2-chloro-2-propenyl ester The title compound is prepared by the procedure of Example 4, using 2.97 g of 4-(1,1-dimethylethyl)phenylsulfinic acid, 2.0 g of 2-chloro-2-propenyl ester, from Example 3, 1.27 g of iodine, 1.26 g of sodium bicarbonate, 1.23 g of sodium acetate, 50 ml of ethyl acetate and 25 ml of water. The reaction mixture is purified by flash chromatography to give 1.95 g (54%) of white crystalline product.

$^1$H NMR. (CDCl$_3$) δ0.091(s,6H), 0.88(s,6H), 1.25(d,3H), 1.36(s,9H), 3.20(m,H), 3.31(m,H), 3.91(q,2H), 4.21 (m,2H), 4.71(s,2H), 5.46(d,2H), 7.12(s,H), 7.59(d,H), 7.81(d,H).

EXAMPLE 4C

[2R-[2Alpha(E),3beta(R*)]]-3-[1-[[(1,1-dimethylethyl)-
dimethylsilyl]oxy]ethyl]- 2-[2-iodo-3-
(2-thienylsulfonyl)-2-propenyl]-4-oxo-1-azetidineacetic
acid, (4-nitrophenyl)methyl ester The title compound is prepared by the procedure of Example 4, using 6.63 g of 2-thiophene sulfinic acid, 5.13 g of the (4-nitrophenyl)methyl ester from Example 3A, 2.81 g of iodine, 1.87 g of sodium bicarbonate, 3.19 g of sodium acetate, 200 ml of ethyl acetate and 50 ml of water. The reaction mixture is purified by chromatography to give 4.21 g (57%) of the desired product.

$^1$H NMR (CDCl$_3$) δ0.07(d,6H), 0.87(s,9H), 1.24(d,3H), 3.21(m,H), 3.29(m,H), 3.80(m,H), 4.03(q,2H), 4.18 (m,2H), 5.27(s,2H), 7.18(m,2H), 7.53(d,2H), 7.70(m,H), 7.78(m,H), 8.23(d,2H).

IR (KBr) 1755 cm$^{-1}$.

EXAMPLE 5

[5R-[5Alpha,6alpha(R*)]]-3-[[(2,4-difluorophenyl)-
sulfonyl]methylene]-
6-[1-[[(1,1-dimethylethyl)dimethylsilyl]oxy]ethyl]-
7-oxo-1-azabicyclo[3.2.0]-heptane- 2-carboxylic
acid, 2-chloro-2-propenyl ester and
[5R-[5alpha,6alpha(R*)]]-3-[[2,4-difluorophenyl)-
sulfonyl]methyl]-6-[1-[[1,1-dimethylethyl)dimethyl-
silyl]oxy]ethyl]-7-oxo-1-azabicyclo[3.2.0]hept-2-ene-
2-carboxylic acid, 2-chloro-2-propenyl ester Four and twenty-three hundreths gram of iodosulfone prepared in Example 4 is dissolved in 45 ml of anhydrous tetrahydrofuran, under argon, and the solution is cooled to −80° C. (ether/dry ice bath). To this solution is added, over a ten minute period, 7.8 ml of a 1M solution of lithium bis(trimethylsilyl)amide in tetrahydrofuran. The resulting yellow solution is stirred at −80° C. for one and a half hours, under argon, and then quenched with 0.53 ml of acetic acid. After 5 minutes of stirring, 2.1 ml of a 0.5 molar solution of potassium dihydrogen phosphate is added and the cooling bath is removed. The solution is warmed to −20°–0° C. and an additional 20 ml of 0.5 molar solution of potassium dihydrogen phosphate is added followed by 75 ml of ethyl acetate. The aqueous phase is separated, washed with 3×75 ml of ethyl acetate and the wash is combined with the organic phase of the reaction mixture. The combined organic phase is washed with 75 ml of water and 75 ml of brine. The organic phase is dried over magnesium sulfate and evaporated to give, after flash column chromatography (20% ethyl acetate/hexane), 1.13 g (33%) of the endocyclic product and 1.8 g (52%) of the exocyclic product.

$^1$H NMR (endo) (CDCl$_3$) δ0.071(d,6H), 0.879(s,9H), 1.24 (d,3H), 3.23(m,2H), 4.25(m,2H), 4.56(q,2H), 4.62 (s,2H), 5.36(s,H), 5.57(d,H), 6.94(m,H), 7.03(m,H), 7.89(m,H).

$^1$H NMR (exo) (CDCl$_3$) δ0.061(d,6H), 0.87(s,9H), 1.22 (d,3H), 2.99(m,2H), 3.10(m,H), 3.77(m,H), 4.39(m,H), 4.79(q,2H), 5.22(s,H), 5.43(d,H), 5.63(d,H), 6.5 (s,H), 7.02(m,2H), 7.93(m,H).

EXAMPLE 5A

[5R-[3E,5Alpha,6alpha(R*)]]-3-[[(3,4-dimethoxy-
phenyl)sulfonyl]methylene]-
6-[1-[[(1,1-methylethyl)dimethylsilyl]oxy]ethyl]-
7-oxo-1-azabicyclo[3.2.0]-heptane- 2-carboxylic
acid, 2-chloro-2propenyl ester The title compound is prepared by the procedure of Example 5, using 5.7 g of iodo-sulfone from Example 4A, 60 ml of anhydrous tetrahydrofuran, 10.2 ml of 1M solution of lithium bis(trimethylsilyl)amide in tetrahydrofuran, 0.7 ml acetic acid and 2.8 ml+26 ml of 0.5M potassium dihydrogen phosphate. The reaction mixture is purified by chromatography to give 3.02 g (64%) of the pure exocyclic product as a white solid.

$^1$H NMR (CDCl$_3$) δ0.066(s,6H), 0.873(s,9H), 1.22(d,3H), 2.87(m,H), 2.94(d,H), 2.96(d,H), 3.76(m,H), 3.95 (d,6H), 4.17 (m,H), 4.70(d,H), 4.89(d,H), 5.30(s,H), 5.42(s,H), 5.73(s,H), 6.36(s,H), 6.98 (d,H), 7.29 (d,H), 7.5(d,2H).

CI-MS: m/z 617(M+NH$_3$)$^+$.

EXAMPLE 5B

[5R-[3E,5Alpha,6alpha(R*)]]-6-[1-[[(1,1-dimethyl-
ethyl)dimethylsilyl]oxy]ethyl]3-[[[4-(1,1-dimethyl-
ethyl)phenyl]sulfonyl]methylene]-7-oxo-1-azabicyclo-
[3.2.0]-heptane-2-carboxylic acid,
2-chloro-2-propenyl ester The title compound is prepared by the procedure of Example 5, using 6.18 g of the iodo-sulfone from Example 4B, 64 ml of anhydrous tetrahydrofuran, 11.1 ml of 1M solution of lithium bis(trimethylsilyl)amide in tetrahydrofuran, 0.75 ml acetic acid, and 3 ml 28.5 ml of 0.5M potassium dihydrogen phosphate. The reaction mixture is purified by chromatography to give 1.5 g (15%) of pure exocyclic product as a white solid.

$^1$H NMR (CDCl$_3$) δ0.062(s,6H), 0.871(s,9H), 1.22(d,3H), 1.34(s,9H), 2.79(m,H), 2.82(d,H), 2.86(d,H), 2.95 (d,H), 3.75(m,H), 4.17(m,H), 4.79(q,2H), 5.29(s,H), 5.43(s,H), 5.68(s,H), 6.39(s,H), 7.56(d,2H), 7.77 (d,2H).

EXAMPLE 5C

[2R-[2Alpha,3Z,5alpha,6alpha(R*)]]-6-[1-[[(1,1-
dimethylethyl)dimethylsilyl] oxy]ethyl]-7-oxo-
3-[2-thienylsulfonyl)methylene]-1-azabicyclo[3.2.0]-
heptane-2-carboxylic acid, (4-nitrophenyl)methyl
ester The title compound is prepared by the procedure of Example 5, using 4.1 g of the iodo-sulfone from Example 4C, 50 ml of anhydrous tetrahydrofuran, 7.25 ml of 1M solution of lithium bis(trimethylsilyl)amide in tetrahydrofuran, 0.59 ml of acetic acid and 2 ml+20 ml of 0.5M potassium dihydrogen phosphate. The reaction mixture is purified by chromatography to give 1.85 g of desired product as a white solid, m.p. 157°–159° C.

$^1$H NMR (CDCl$_3$) δ0.071(d,6H), 0.876(s,9H), 1.23(d, 3H), 2.84(m,H), 2.91(m,H), 2.98(m,H), 5.25(m,H), 5.38(d, H), 6.49(m,H), 7.12(m,H), 7.58(m,H), 7.67(m,2H), 7.1(m, H), 8.21(m,2H).

IR (KBr) 1744, 1771 cm$^{-1}$.

EXAMPLE 6

[5R[5Alpha,6alpha(R*)]]-3-[[2,4-difluorophenyl)-
sulfonyl]methyl]-6-(1-hydroxyethyl)-7-oxo-1-aza-
bicyclo[3.2.0]hept-2-ene-2-carboxylic acid,
2-chloro-2-propenyl ester To a solution of 1 g of the endocyclic product prepared in Example 5 in 33 ml of anhydrous tetrahydrofuran is added 8.7 ml of a molar solution of tetrabutylammonium fluoride in tetrahydrofuran and 1.5 ml of acetic acid. The reaction mixture is stored overnight in the refrigerator and then diluted with 20 ml of cold ethyl acetate. The organic phase is washed with 2×20 ml of cold water, 20 ml of cold 10% aqueous sodium bicarbonate solution and 20 ml of cold brine. The organic layer is dried over magnesium sulfate and evaporated without heating to give 0.80 g of crude product.

EXAMPLE 7

[5R-[3E,5Alpha,6alpha(R*)]]-3-[[(3,4-dimethoxyphenyl)sulfonyl]methylene]-6-(1-hydroxyethyl)-7-oxo-1-azabicyclo[3.2.0]heptane-2-carboxylic acid, 2-chloro-2-propenyl ester One and two tenths grams of exocyclic product prepared in Example 5A is dissolved in 11.6 ml of acetonitrile. The solution is added to a polyethylene bottle containing 4.4 ml of 50% aqueous hydrogen fluoride and 39 ml of acetonitrile. After two hours of stirring at room temperature, 12–13 g of solid sodium bicarbonate is added until a pH of 7–8 is reached. The solids are then filtered and the acetonitrile is stripped under reduced pressure. The aqueous solution is extracted with 2×50 ml of ethyl acetate. The combined organic phase is washed with 50 ml of water, 50 ml of brine and dried over magnesium sulfate. The solid is filtered and the filtrate is evaporated to dryness to give 0.568 g (60.4%) of product after flash column chromatography (ethylacetate system).

$^1$H NMR (CDCl$_3$) δ1.33(d,3H), 1.77(d,OH), 2.8(m,H), 2.94 (d,H), 3.03(d,H), 3.79(m,H), 3.95(d,6H), 4.21(m,H), 4.80(d,2H), 5.3(s,H), 5.43(s,H), 5.73(s,H), 6.38(s,H), 6.96(d,H), 7.29(s,H), 7.49(d,H).

EXAMPLE 7A

[5R-[3E,5Alpha,6alpha(R*)]]-3-[[[4-(1,1-dimethylethyl)phenyl]sulfonyl]methylene]-6-(1-hydroxyethyl)-7-oxo-1-azabicyclo[3.2.0]heptane-2-carboxylic acid, 2-chloro-2-propenyl ester The title compound is prepared by the procedure of Example 7, using 1.5 g of the exocyclic product from Example 5B, 15 ml of acetonitrile, 5.5 ml of 50% aqueous hydrogen fluoride in 49 ml of acetonitrile and excess sodium bicarbonate (to pH 7–8). 0.994 g (83%) of product is isolated without further purification. CI-MS: m/z 499(M+NH$_4$)$^+$ and 482(M+H)$^+$.

EXAMPLE 8

[5R-[5Alpha,6alpha(R*)]]-3-[[(3,4,-dimethoxyphenyl)sulfonyl]methyl]-6-(1-hydroxyethyl)-7-oxo-1-azabicyclo[3.2.0]hept-2-ene-2-carboxylic acid, 2-chloro-2-propenyl ester A solution of 0.568 g of exocyclic product from Example 7 and 3.4 ml of diisopropylethylamine in methylene chloride is stirred for 3 hours at room temperature and in the refrigerator for two days. The solution is then evaporated to dryness without heating to give 0.363 g (64%) of product after flash column chromatography (cold ethyl acetate as eluding system).

EXAMPLE 8A

[5R-[5Alpha,6alpha(R*)]]-3-[[[4-(1,1-dimethylethyl)phenyl]sulfonyl]methyl]-6-(1-hydroxyethyl)-7-oxo-1-azabicyclo[3.2.0]hept-2-ene-2-carboxylic acid, 2-chloro- 2-propenyl ester The title compound is prepared by the procedure of Example 8, using 0.97 g of exocyclic product from Example 7A, 5.8 ml of diisopropylethylamine and 6.8 ml of methylene chloride. 0.66 g (68%) of product is isolated without further purification.

EXAMPLE 9

[5R-[5Alpha,6alpha(R*)]]-3-[[(2,4-difluorophenyl)sulfonyl]methyl]-6-(1-hydroxyethyl)-7-oxo-1-azabicyclo[3.2.0]hept-2-ene-2-carboxylic acid, monopotassium salt To a solution of 0.80 g of product prepared in Example 6 in 10 ml of ethyl acetate and 10 ml of methylene chloride is added, under argon, 0.040 g of triphenylphosphine, 13.3 ml of 0.13 molar potassium 2-ethylhexanoate in ethyl acetate and 0.066 g of tetrakis(triphenylphosphine)palladium catalyst. The reaction mixture is stirred at room temperature for 2 hours and evaporated to dryness without heating. It is purified by reverse phase thin layer chromatography (water/ethanol:95/5) to give 0.0655 g (20.7%) of product as the potassium salt.

$^1$H NMR (D$_2$O) δ1.27(d,3H), 3.09(m,2H), 3.41(m,H), 4.20 (m,2H), 4.64(d,H), 4.95(d,2H), 7.21(m,2H), 7.90(m, H).

EXAMPLE 9A

[5R-[5Alpha,6alpha(R*)]]-3-[[(3,4-dimethoxyphenyl)sulfonyl]methyl]-6-(1-hydroxyethyl)-7-oxo-1-azabicyclo]3.2.0]hept-2-ene-2-carboxylic acid, monopotassium salt The title compound is prepared by the procedure of Example 9, using 0.366 g of the endocyclic product from Example 8, 4.5 ml of ethyl acetate, 4.5 ml of methylene chloride, 0.027 g of triphenylphosphine, 0.237 g of potassium 2-ethylhexanoate and 0.045 g of tetrakis(triphenylphosphine)palladium catalyst. 0.828 g (25%) of product is isolated after reverse phase thin layer chromatography (water/ethanol:95/5) .

$^1$H NMR (D$_2$O) δ1.26(d,3H), 2.97(m,2H), 3.33(m,H), 3.95 (d,6H), 4.1(m,H), 4.2(m,H), 4.54(d,H), 4.91(d,H), 7.18 (d,H), 7.36(d,H), 7.51(d,H).

EXAMPLE 9B

[5R-[5Alpha,6alpha(R*)]]3[[[4(1,1-dimethylethyl)phenyl]sulfonyl]methyl]-6-(1-hydroxyethyl)-7-oxo-1-azabicyclo[ 3.2.0]hept-2-ene-2-carboxylic acid, monopotassium salt The title compound is prepared by the procedure of Example 9, using 0.660 g of the endocyclic product from Example 8A, 8 ml of ethyl acetate, 8 ml of methylene chloride, 0.52 g of triphenylphosphine, 0.278 g of potassium 2-ethylhexanoate and 0.052 g of tetrakis(triphenylphosphine)palladium catalyst. 0.1194 g (20%) of product is isolated after reverse phase thin layer chromatography (water/ethanol 75/25).

$^1$H NMR (D$_2$O) δ1.25(d,3H), 1.34(s,9H), 2.92(m,2H), 3.31 (m,H), 4.1(m,H), 4.2(m,H), 4.56(d,H), 4.9(d,H), 7.70 (d,2H), 7.80(d,2H).

EXAMPLE 10

[5R-[5Alpha,6alpha(R*)]]-6-(1-hydroxyethyl)-3-[(2-thienylsulfonyl)methyl]-7-oxo-1-azabicyclo[3.2.0]-hept-2-ene-2-carboxylic acid, monosodium salt Following the procedure of Example 7, 0.614 g of the exocyclic product of Example 5C, 10 ml of acetonitrile, 8 ml of 50% aqueous hydrogen fluoride in 42 ml of acetonitrile and excess sodium bicarbonate (to pH 7–8) is reacted. 0.405 g (81%) of the desired product is obtained and used in the following reaction without purification.

To a solution of 15 ml of methylene chloride and 15 ml diisopropylethylamine is added 0.400 g of the above alcohol. The reaction is stored at 4° C. for 17 hours. The solution is concentrated to dryness, extracted with ethyl acetate and washed with 0.5N potassium hydrogen phosphate until neutral. The organic layer is dried with sodium sulfate, filtered and concentrated to give 0.370 g of desired product.

To a solution of 0.370 g of the endocyclic alcohol from above in 3.15 ml of water and 17.68 ml of dioxane is added 0.0682 g of sodium bicarbonate and 0.130 g of palladium hydroxide. The reaction is hydrogenated on a Parr shaker for 1 hour at 20 psi, filtered through diatomaceous earth and washed with water. The filtrate is concentrated, extracted with diethyl ether and the aqueous phase is lyophilized. The resulting solid is purified by reverse-phase chromatography (5% ethanol:water, v:v) to give 0.045 g (26%) of the desired product.

$^1$H NMR (D$_2$O) δ1.28(d,3H), 3.04(m,2H), 3.42(m,H), 4.20 (m,2H), 4.7(m,2H), 7.27(t,H), 7.71(d,H), 7.92(m,H).

EXAMPLE 11

[2R-[2Alpha(E),3beta(R*)]]-3-[1-[[(1,1-dimethylethyl)-dimethylsilyl]oxy]ethyl]-2-[2-iodo-3-[(4-methylphenyl)-sulfonyl]-2-propenyl]-4-oxo-1-azetidineacetic acid, (4-methoxyphenyl)methyl ester The title compound is prepared by the procedure of Example 4, 0.87 g of the p-methoxybenzyl ester from Example 23, 0.63 g of sodium 4-toluenesulfinate dihydrate, 0.50 g of iodine, 0.25 g of sodium acetate in 12 ml of ethyl acetate and 6 ml of water is irradiated with a 300 W bulb for 45 minutes. After purification, 1.04 g (73%) of product is obtained as an oil.

$^1$H NMR (CDCl$_3$) δ0.1(s,6H,2CH$_3$), 0.9(s,9H,3CH$_3$), 1.25 (d,3H,CH$_3$), 2.45(s,3H,CH$_3$), 3.18(dd,1H,H$_3$), 3.25 (dd,1H,allylic H), 3.75(dddd,1H,allylic H), 3.8 (s,3H, CH$_3$O), 3.9(dd,2H,CH$_2$CO$_2$), 4.15(m,2H,CHOSi,H$_4$), 5.1(dd,2H,CH$_2$O), 6.87(d,2H,aromatic), 7.1(s,1H,vinyl H), 7.3(d, 2H, aromatic), 7.38 (d, 2H, aromatic), 7.8 (d, 2H, aromatic).

IR (neat) 1738, 1753 cm$^{-1}$.

EXAMPLE 12

[5R-[5Alpha,6alpha(R*)]]-3-[[(4-methylphenyl)-sulfonyl]-methyl]-6-[1-[[(1,1-dimethylethyl)dimethyl-silyl]oxy]-ethyl]-7-oxo-1-azabicyclo[3.2.0]hept-2-ene-2-carboxylic acid, (4-methoxyphenyl)methyl ester and
[5R-[3E,5Alpha,6alpha(R*)]]-3-[[(4-methylphenyl)-sulfonyl]methyl]-6-[1-[[(1,1dimethylethyl)dimethyl-silyl]oxy]ethyl]-7-oxo-1-azabicyclo[3.2.0]heptane-2-carboxylic acid, (4-methoxyphenyl)methyl ester The title compounds are prepared by the procedure of Example 5, using 2.3 g of iodo-vinyl sulfone from Example 11, 25 ml of anhydrous tetrahydrofuran and 4.7 ml of a 1M solution of lithium bis(trimethylsilyl)amide in tetrahydrofuran. The product, as an oil, consists of a mixture of the 2 isomers weighing 1.0 g after purification by flash column chromatography.

EXAMPLE 13

[2R-[2Alpha,3E,5alpha,6alpha(R*)]]-6-(1-hydroxy-ethyl)-3-[[(4-methylphenyl)sulfonyl]methylene]-7-oxo-1-azabicyclo[ 3.2.0]heptane-1-carboxylic acid, (4-methoxyphenyl)methyl ester A 0.450 g sample of the isomeric mixture prepared in Example 12 is dissolved in a solution of 13 ml of tetrahydrofuran and 0.63 ml of acetic acid. To this is added 3.6 ml of 1M tetra-n-butylammonium fluoride/tetrahydrofuran solution according to the procedure outlined in *J. Med. Chem.* (1987) 30,879. After the prescribed workup and purification, 0.244 g (67%) of product is obtained as an oil.

$^1$H NMR (CDCl$_3$) δ1.3(d,3H,CH$_3$), 2.42(s,3H,CH$_3$), 2.78(m, 1H,allylic H), 2.9(dd, 1H,allylic H), 3.02(dd,1H, H$_6$), 3.75(m, 1H,H$_5$), 3.8(s,3H,CH$_3$O), 4.2(p,1H,CHO), 5.21(s,2H,CH$_2$CO$_2$), 5.23(s,1H,H$_3$), 6.35(s,1H,vinyl H), 6.9(d,2H,aromatic), 7.3(d,2H,aromatic), 7.4 (d,2H, aromatic), 7.65 (d, 2H, aromatic).

IR (KBr) 3448, 3038, 2968, 1765, 1740 cm$^{-1}$.

EXAMPLE 14

[2R-[2Alpha,3E,5alpha,6beta(R*)]]-6-(1-hydroxyethyl)-3[[4-methylphenyl)sulfonyl]methylene]-7-oxo-1-azabicyclo[ 3.2.0 ]heptane-2-carboxylic acid, monosodium salt Applying the same experimental conditions as in Example 28 as well as that detailed in *J. Org. Chem.* (1984), 49, 5271, 0.20 g of the carbapenem ester prepared in Example 13 is dissolved in 2.6 ml of anisole and 1 ml of methylene chloride at −50° under an inert atmosphere. To this is added 0.190 g of anhydrous aluminum chloride. The reaction product is isolated as its sodium salt and weighs 0.044 g (27%).

1H NMR (D$_2$O) δ1.27(d,3H,CH$_3$), 2.45(s,3H,CH$_3$), 2.8(m,1H,allylic H), 3.0(dd, 1H,allylic H), 3.78(m,1H,CH—N), 4.22(p,1H,CH—O), 6.62(s,1H,vinyl H), 7.5 (d, 2H, aromatic), 7.82 (d, 2H, aromatic).

IR (KBr) 3427, 2970, 2923, 1742, 1623 cm$^{-1}$.

EXAMPLE 15

[5R-[5Alpha,6alpha(R*)]]-6-(1-hydroxyethyl)-3-[[(4-methylphenyl)sulfonyl]methyl]-7-oxo-1-azabicyclo[3.2.0]hept-2 -ene-2-carboxylic acid, (4 -methoxyphenyl)methyl ester The title compound is prepared by the procedure of Example 8, reacting 0.283 g of the carbapenem ester prepared in Example 13, with 2.0 ml of diisopropylethylamine in 5 ml of methylene chloride for 16 hours at 45° C. to give 0.110 g of the product (39%) after purification.

$^1$H NMR (CDCl$_3$) δ1.32(d,3H,CH$_3$), 1.8(d,1H,OH), 2.4(s, 3H,CH$_3$), 3.05(dd,1H,allylic H), 3.2(dd, 1H,H$_6$), 3.3(dd,1H, allylic H), 3.8(s,3H,OCH$_3$), 4.2(m,2H,CHN,CHO), 4.27(d, 1H,CHSO$_2$), 4.67(d,1H,CHSO$_2$), 4.96(dd,2H,CH$_2$O), 6.8(d, 2H,aromatic), 7.35(m,4H,aromatic), 7.7(d,2H,aromatic).

IR (KBr) 3440, 2967, 2839, 1779, 1715 cm$^{-1}$.

EXAMPLE 16

[5R-[5Alpha,6alpha(R,*)]]-6-(1-hydroxyethyl)-3-[[4-methylphenyl)sulfonyl]methyl]-7-oxo-1-azabicyclo-3.2.0]hept-2-ene-2-carboxylic acid, monosodium salt The title compound is prepared by the procedure of Example 14, 0.10 g of the carbapenem ester prepared in Example 15 is hydrolyzed to give 0.030 g (38%) of product as the sodium salt.

hu 1H NMR (D$_2$O) δ1.12(d,3H,CH$_3$), 2.23(s,3H,CH$_3$), 2.93(dd, 1H,allylic H), 3.04(dd,1H,allylic H), 3.35(dd, 1H,H$_6$), 4.12(m,1H,H$_5$), 4.2(p,1H,CHO), 4.55(d,1H, CHSO$_2$), 4.88(d,1H,CHSO$_2$), 7.43(d,2H,aromatic), 7.75 (d,2H,aromatic).

IR (KBr) 3420, 2960, 1760, 1600 cm$^{-1}$.

EXAMPLE 17

[2R-[2Alpha(E), 3beta(R*)]]-2-[3-[[-4-(acetylamino)phenyl]sulfonyl]-2-iodo-2-propenyl]-3-[1-[[(1,1-dimethylethyl)-dimethylsilyl] oxy]ethyl]-4-oxo-1-azetidineacetic acid, 2-chloro-2-propenyl ester The title compound is prepared by the procedure of Example 4, using 1.4 g of the 2-chloroallyl ester from Example 3, 1.4 g of 4-acetamidobenzenesulfinic acid, 0.89 g of iodine, 0.30 g of sodium bicarbonate and 0.89 g of sodium acetate in 20 ml of ethyl acetate and 10 ml of water. After purification, 1.85 g (73%) of product is obtained as an oil.

$^1$H NMR (CDCl$_3$) δ0.09(s,6H,2CH$_3$), 0.9(s,9H,C(CH$_3$)$_3$), 1.2(d,3H,CH$_3$), 2.2(s,3H,CH$_3$), 3.2(dd,1H,H$_3$), 3.35(dd, 1H,allylic CH), 3.7 (dd,1H,allylic CH), 3.95(q,2H, CH$_2$CO$_2$), 4.22(m,2H,CHOSi,H$_4$), 4.7(s,2H,allylic CH$_2$), 5.43(d,1H,vinyl H), 5.5(d,1H,vinyl H), 7.1(s,1H,vinyl H), 7.75(d,2H,aromatic), 7.8(d,2H,aromatic), 7.77(bs,1H,NH).

EXAMPLE 18

[5R-[3E, 5Alpha,6alpha(R*)]]-3-[[4-acetamidophenyl)-sulfonyl] methylene]-6-[[(1,1-dimethylethyl)dimethylsilyl] oxy]ethyl]-7-oxo-1-azabicyclo[3.2.0]-heptene-2-carboxylic acid, 2-chloro-2-propenyl ester The title compound is prepared by the procedure of Example 5, using 1.78 g of the iodovinyl sulfone from Example 17, 18 ml of anhydrous tetrahydrofuran and 5.7 ml of a 1M solution of lithium bis(trimethylsilyl)amide in tetrahydrofuran. After purification, 0.25 g (17%) of the product is obtained.

$^1$H NMR (CDCl$_3$) δ0.1(s,6H,2CH$_3$), 0.75(s,9H,C(CH$_3$)$_3$), 1.25(d,3H,CH$_3$), 2.2(s,3H,CH$_3$), 3.2(m,3H,allylic CH$_2$ and H$_6$), 4.2(m,1H,H$_5$), 4.5(q,2H,allylic CH$_2$), 5.35(s,1H, vinyl H), 5.65(s,1H,vinyl H), 7.48 (bs,1H,NH), 7.65(d,2H,aromatic), 7.75(d,2H, aromatic).

EXAMPLE 19

[5R-[3E,5Alpha,6alpha(R*)]]-3-[[4-acetamidophenyl)-sulfonyl] methylene]-6-[1-hydroxyethyl]-7-oxo-1-azabicyclo-[3.2.0]heptene-2-carboxylic acid, 2-chloro-2,propenyl ester The title compound is prepared by the procedure of Example 6, reacting 0.251 g of the carbapenem from Example 18, 8 ml anhydrous tetrahydrofuran, 0.37 ml of acetic acid, 2.1 ml of a 1M solution of tetra-n-butylammonium fluoride in tetrahydrofuran for 7 hours at 20° under an inert atmosphere; then storing overnight at 4° C. The reaction is purified to give 0.115 g (57%) of desired product and 0.042 g of unreacted starting material.

$^1$H NMR (CDCl$_3$) δ1.3(d,3H,CH$_3$), 2.2(s,3H,CH$_3$), 2.3(bs,1H,OH), 3.1(dd,1H,allylic H), 3.25(dd,1H,H$_6$), 3.35(dddd,1H,allylic H), 4.2(m,2H,CHO and H$_5$), 4.4(dd, 2H,CH$_2$), 4.65(t,2H,CH$_2$), 5.4(d,1H,vinyl H), 5.6(d,1H,vinyl H), 7.8(m,4H,aromatic), 9.35(s,1H,NH).

IR (KBr) 3492 (OH,NH), 1811, 1729, 1640 cm$^{-1}$.

EXAMPLE 20

[5R-[5Alpha,6alpha(R*)]]-3-[[4-acetamidophenyl)-sulfonyl]methylene]-6-[1-hydroxyethyl]-7-oxo-1-azabicyclo[3.2.0]heptane-2-carboxylic acid, monopotassium salt The title compound is prepared by the procedure of Example 9 and in *J. Med. Chem.* (1987) 30, 879, using 0.105 g of the hydroxyethyl carbapemen from Example 19, 0.013 g of tetrakis(triphenylphosphine) palladium, 0.006 g of triphenylphosphine, 0.045 g of potassium 2-ethylhexanoate in 2 ml of ethyl acetate and 2 ml of water. The reaction mixture, after work up, gives 0.040 g (41%) of desired product.

$^1$H NMR (D$_2$O) δ1.25(d,3H,CH$_3$), 2.2(s,3H,CH$_3$), 3.0 (dddd,2H,allylic CH$_2$), 3.37(dd,1H,H$_6$), 4.15(m,3H,CH—O, H$_4$ and CHSO$_2$), 4.52 (d, 1H, CHSO$_2$), 7.78 (dd, 4H, aromatic).

IR (KBr) 3418 (broad), 1760, 1687, 1591 cm$^{-1}$.

EXAMPLE 21

[2R-[2Alpha,3beta(R*)]]-3-[1-[[(1,1-dimethyl)-dimethylsilyloxy]ethyl]-2-(4-methoxy-4-oxo-2-butynyl)-4-oxo- 1-azetidineacetic acid, (4-nitrophenyl)methyl ester To a 50 ml methanolic solution containing 2.5 g of the acetylenic ester prepared in Example 3A is added 0.1 gm palladium chloride, 1.6 g anhydrous cupric chloride and 1.1 g sodium acetate. The reaction solution is degassed 3 times using carbon monoxide. Then the reaction flask is fitted with a balloon containing approximately 300 ml gaseous carbon monoxide. The reaction is stirred under this carbon monoxide atmosphere until the green reaction color turns to black. Tlc monitoring indicates all starting acetylene to be consumed. The reaction mixture is poured over a mixture of ice water and diethyl ether. Following an aqueous workup and purification via flash column chromatography, a colorless crystalline material 2.0 g (71%) is isolated, m.p. 55° C.

$^1$H NMR (CDCl$_3$) δ0.01(s,3H,CH$_3$), 0.04(s,3H,CH$_3$), 0.84(s,9H,t-Bu), 1.24(d,3H,CH$_3$), 2.7(m,2H,propargyl CH$_2$), 2.9(dd,1H,H$_3$), 3.73(s,3H,OCH$_3$), 4.0(m, 1H$_4$), 4.13(dd,2H,CH$_2$), 4.3(m, 1H,CH—O—Si), 5.25(s,2H,benzylic CH$_2$), 7.53(d,2H,aromatic), 8.25(d,2H,aromatic).

Anal for C$_{25}$H$_{34}$N$_2$O$_8$Si:C, 57.90; H, 6.61; N, 5.40. Found: C, 57.57; H, 6.56; N, 5.35.

EXAMPLE 22

[2R-[2Alpha(E),3beta (R*)]]-2-(2,3-dichloro-4-methoxy-4-oxo-2-butenyl)-3-[1-[[1,1-dimethylethyl)dimetylsilyl]oxy]ethyl]-4-oxo-1-azetidineacetic acid, (4-nitrophenyl)methyl ester A mixture containing 0.11 gm of the acetylenic methyl ester prepared in Example 21, 0.54 g cupric chloride, 0.16 g lithium chloride and 6 ml of acetonitrile is heated at 80° C. until the starting acetylene is consumed (by Tlc analysis). The reaction is cooled and then filtered through diatomaceous earth to remove all solids. Diethyl ether and water are added to the filtrate followed by an aqueous workup. Purification via flash column chromatography gives 0.086 g (73%) product as a colorless solid, m.p. 73°–75° C.

$^1$H NMR (CDCl$_3$) δ0.05(s,3H,CH$_3$), 0.07 (s,3H,CH$_3$), 0.85(s,9H,C(CH$_3$)$_3$), 1.25(d,3H,CH$_3$), 3.1(m,2H,allylic CH$_2$), 3.03(dd,1H,H$_3$), 3.85(s,3H,CH$_3$O), 4.05(ab quartet, 2H,CH$_2$), 4.2(m,2H,CH—O,H$_4$), 5.25(s,2H,CH$_2$CO$_2$), 7.5 (d, 2H, aromatic), 8.25 (d,2H, aromatic).

Anal. for C$_{25}$H$_{34}$Cl$_2$N$_2$O$_8$Si: C, 50.93; H, 5.81; N, 4.75; Cl, 12.03. Found: C, 51.34; H, 5.76; N, 4.65; Cl, 11.97.

EXAMPLE 23

[3S-[3Alpha(S*),4beta]]-3-[1-[[(1,1-dimethylethyl)-dimethylsilyl]oxy]ethyl]-2-oxo-4-(2-propynyl)-1-azetidineacetic acid, (4-methoxyphenyl)methyl ester To a suspension of 0.164 g of prewashed sodium hydride (60% in oil) in 5 ml of anhydrous tetrahydrofuran is added, with stirring under argon, a solution of 1.0 g of the azetidinone, from Example 1, in 6 ml of anhydrous tetrahydrofuran at −20° C. The mixture is stirred for 10 minutes at 0° C., followed by the addition at −20° C. of 1.065 g of (4-methoxyphenyl)methyl bromoacetate in anhydrous tetrahydrofuran and the reaction is stirred at 0° C. for 17 hours. A 2 ml solution (1 ml glacial acetic acid+9 ml of water) is added to adjust the pH to 4. The mixture is poured over cracked ice, extracted with ethyl acetate and the combined organic layers washed with brine. The organic layer is dried over anhydrous magnesium sulfate and concentrated. The resulting oil is purified by flash chromatography to give 0.799 g (48%) of the desired product, m.p. 54°–57° C.

Calcd. for (C$_{24}$H$_{35}$NO5S, MW 445.6): C, 64.69; H, 7.92; N, 3.14; Si, 6.30. Found: C, 64.37; H, 7.78; N, 3.04; Si, 6.29.

$^1$H NMR (CDCl$_3$) δ0.041(s,3H,CH$_3$—Si), 0.063(s,3H,CH$_3$—Si), 0.856(s,9H, (CH$_3$)$_3$—C), 1.24(d, 3H,CH$_3$CH), 1.97 (m, 1H,C≡CH), 2.56(m,2H,CH$_2$—C≡C), 2.92(m, 1H,O═C—CH—CH—N), 3.81(s,3H,CH$_3$—O), 3.92(m, 1H,O═C—CH—CH—N), 4.05(dd,2H,N—CH$_2$), 4.16(m, 1H,CH$_3$CH—O), 5.10(s,2H,O—CH$_2$-φ), 6.89 (d,2H, CH$_3$O—C—CH), 7.29(d,2H,CH$_3$O—C—CH—CH).

IR (KBr) 1734, 1758 cm$^{-1}$.

EXAMPLE 24

[2R-[2Alpha(E),3beta (R*)]]-3-[1-[[(1,1-dimethylethyl)dimethylsilyl]oxy]-ethyl]-2-[2-iodo-3-(phenylsulfonyl)-2propenyl]-4-oxo-1-azetidineacetic acid, (4-methoxyphenyl)methyl ester The title compound is prepared by the procedure of Example 4, using 3.94 g of the product from Example 23, 2.18 g of sodium benzenesulfinate, 2.24 g of iodine and 1.45 g of sodium acetate. The mixture is purified by chromatography to give 5.29 g (84%) of the desired product as a pale yellow oil.

$^1$H NMR (CDCl$_3$) δ0.070(s,3H,CH$_3$—Si), 0.078(s,3H,CH$_3$—Si), 0.873(s,9H, (CH$_3$)$_3$—C), 1.23(d, 3H,CH$_3$CH), 3.17(m,1H,O═C—CH—CH—N), 3.30(dd, 1H,CHCH$_2$—C≡C), 3.71(dd, 1H,CH—CH$_2$—C≡C), 3–76(s, 1H,N—CH$_2$), 3.80(d, 3H,OCH$_3$), 3.94(s,1H,NCH$_2$), 4.17(m, 1H,O═C—CH—CH—N), 4.17-(m,1H,CH$_3$CH—O), 5.08(2d,2H,O—CH$_2$-φ), 6.87(d, 2H,CH$_3$O—C—CH), 7.10(s,1H,CH—SO$_2$), 7.29(d, 2H,CH$_3$O—C—CH—CH), 7.59(t,2H,S—CH—CH—CH), 7.68(t, 1H,S—CH—CH—CH), 7.90(d,2H,S—CH—CH).

IR (neat) 1742, 1761 cm$^{-1}$.

CI-MS: m/z 714 (M+H)$^+$ and 731 (M+NH$_4$)$^+$.

EXAMPLE 25

[5R-[3E,5Alpha,6alpha(R*)]]-6-[1-[[(1,1-dimethylethyl)dimethylsilyl]oxy] ethyl]7-oxo-3-[(phenylsulfonyl)methylene]-1-azabicyclo[3.2.0]heptane-2-carboxylic acid, (4-methoxyphenyl)methyl ester The title compound is prepared by the procedure of Example 5, using 3.18 g of the product from Example 24, 30 ml of anhydrous tetrahydrofuran, 6.68 ml of 1M lithium bis(trimethylsilyl)amide in tetrahydrofuran, 0.45 ml of glacial acetic acid and 1.5 ml+15 ml of 1M potassium dihydrogen phosphate. The 2.69 g isomeric mixture is slurried with 25% ethyl acetate/hexane to give 0.798 g (30.5%) of the exocyclic product as a white solid. The filtrate is concentrated to give 1.83 g (70%) of the endocyclic product as an oil.

$^1$H NMR (exo) (CDCl$_3$) δ0.064(s,6H, (CH$_3$)$_2$Si), 0.866(s, 9H, (CH$_3$)$_3$C), 1.23(d, 3H, CH$_3$CH), 2.84(m,2H,—CH$_2$—C═CH—S), 2.95 (m, 1H,O═C—CH—CH—N), 3.80(s,3H,OCH$_3$), 4.18(m,1H,CH$_3$CH—O), 5.20(2d,2H, O—CH$_2$—φ), 5.25(s,1H,N—CH—COO), 6.34(s,1H,C═CH—S), 6.88(d,2H,CH$_3$O—C—CH), 7.40(d,2H,CH$_3$O—C—CH—CH), 7.50(t,2H,S—CH—CH—CH), 7.63(t,1H, S—CH—CH—CH), 7.77(d,2H,S—CH—CH).

CI-MS: m/z 586(M+H)$^+$ and 603(M+NH$_4$)$^+$.

Calc'd. for (C$_{30}$H$_{39}$NO$_7$SiS, MW 585.8):C, 61.51; H, 6.71; N, 2.39; Si, 4.79; S, 5.47.

Found: C, 61.78; H, 6.65; N, 2.28; Si, 4.53; S, 5.47.

EXAMPLE 26

[5R-[3(E), 5Alpha, 6alpha (R*).]]-6-(1-hydroxyethyl)-7-oxo-3-[(phenylsulfonyl) methylene]-1-azabicyclo[3.2.0]-heptane-2-carboxylic acid, (4-methoxyphenyl)-methyl ester The title compound is prepared by the procedure of Example 6, using 0.50 g of the product from Example 25, 17 ml of tetrahydrofuran, 4.27 ml of 1M tetrabutylammonium fluoride and 0.74 ml of glacial acetic acid. The mixture is purified by flash chromatography to give 0.148 g (37%) of the desired product.

$^1$H NMR (CDCl$_3$) δ1.30(d,3H,CH$_3$CH), 2.88(m,2H,—CH$_2$—C=CH—S), 3.0(m,1H,O=C—CH—CH—N), 3.80(s, 3H,OCH$_3$), 4.2(m,1H,CH$_3$CH—O), 5.20(2d, 2H,O—CH$_2$—φ), 5.25 (s,1H, N—CH—COO), 6.35(s,1H, C=CH—S), 6.9(d,2H, CH$_3$O—C—CH), 7.4(d, 2H, CH$_3$O—C—CH—CH), 7.52(t,2H,S—CH—CH—CH), 7.65(t,1H,S—CH—CH—CH), 7.77(d,2H, S—CH—CH).

EXAMPLE 27

[5R-[5Alpha, 6alpha (R*) ]]-6-(1-hydroxyethyl)-7-oxo-3-[(phenylsulfonyl)-methyl]-1-azabicyclo [3.2.0]hept-2-ene-2-carboxylic acid, (4-methoxyphenyl)methyl ester The title compound is prepared by a modification of the procedure of Example 8.

A solution of 0.281 g of exocyclic product from Example 26 and 1.72 ml of diisopropylethylamine in 2 ml of methylene chloride is stirred at gentle reflux, under argon, for 13 hours and then stored at 0° C. for 18 hours,. The reaction is diluted with 50 ml of ethyl acetate, washed 4 times with 10 ml of 0.5M potassium hydrogen phosphate and dried over magnesium sulfate. The organic layer is concentrated to give a quantitative yield of the endocyclic product.

$^1$H NMR (CDCl$_3$) δ1.34(d,3H,CH$_3$—CH), 3.08(2d,1H, —CH$_2$—C—CH$_2$—SO$_2$—), 3.20(m, 1H,O=C—CH—CH—N), 3.31(2d,1H,—CH$_2$—C—CH$_2$—SO$_2$—), 3.81(s,3H,OCH$_3$), 4.22(m,1H,CH$_3$CH—O), 4.22(m,1H, O=C—CH—CH—N), 4.31(d, 1H,—CH$_2$—SO$_2$), 4.66(d, 1H, —CH$_2$—SO$_2$), 4.94( 2d,2H,O—CH$_2$—φ), 6.89(d,2H, CH$_3$O—C—CH), 7.28(d,2H,CH$_3$O—C—CH—CH), 7.46(t, 2H,S—CH—CH—CH), 7.56(t,1H,S—CH—CH—CH), 7.78(d,2H,S—CH—CH).

IR (neat) br. 1729 cm$^{-1}$.
CI-MS: m/z 489 (M+NH$_4$)$^+$.

EXAMPLE 28

[5R-[5Alpha, 6alpha (R*)]]-6-1-hydroxyethyl-7-oxo-3-[phenylsulfonyl) methyl]-1-azabicyclo[3.2.0]hept-2-ene-2-carboxylic acid, monosodium salt To a stirred solution, under argon, of 0.132 g of product from Example 27 in 2.24 ml of anisole and 0.56 ml of methylene chloride is added, at −60° C., 0.0955 g of sublimed aluminum trichloride. The reaction mixture is stirred at −60° C. for 1 hour. Eight and four tenths ml of 5% sodium bicarbonate is added at −60° C., followed by 25 ml of ethyl acetate. The reaction mixture is allowed to warm to room temperature and filtered. The collected solid is washed with ethyl acetate and water. The organic layer is washed with water and the combined water layers are washed with 20 ml of ethyl acetate. The aqueous layer is chromatographed to give 0.074 g (71%) of the desired product.

$^1$H NMR (D$_2$O) δ1.27(d,3H,CH$_3$—CH), 2.96(2d, 1H,—CH$_2$—C—CH$_2$—SO$_2$), 3.07 (2d, 1H,—CH$_2$—C—CH$_2$—SO$_2$), 3.36(m, 1H,O=C—CH—CH—N), 4.13(m, 1H,O=C—CH—CH—N), 4.19 (m, 1H,CH$_3$CH—O), 4.78(2d,2H,CH$_2$—SO$_2$), 7.64(t2H, S—CH—CH), 7.79(t,1H, S—CH—CH—CH), 7.88(d,2H S—CH—CH).

IR (KBr)1756 cm$^{-1}$.
CI-MS: m/z 391(M+NH$_4$)$^+$.

Example 29

[2R-[2Alpha(Z),3beta(R*)]]-3-[1-[[(1,1-dimethylethyl)-dimethylsilyl]oxy]ethyl]-2-[2-iodo-3-[[4-(trifluoromethyl)phenyl]sulfonyl]-2-propenyl]-4-oxo-1-azetidineacetic acid, (4-nitrophenyl)methyl ester The title compound is prepared by the procedure of Example 4, using 4.6 g of the 4-nitrobenzyl ester prepared as described in Example 3A, 4.2 g of 4-(trifluoromethyl-)benzenesulfinic acid, 1.5 g of sodium acetate, 0.84 g of sodium bicarbonate, 2.0 g of iodine, 75 ml of ethyl acetate and 35 ml of water. The mixture is purified by=chromatography to give 7.7 g (95%) of the desired product.

$^1$H NMR (CDCl$_3$) δ0.067(d,6H), 0.087(s,9H), 3.25(t,1H), 3.27(m, 1H), 3.76(q, 1H), 4.04–4.17(m,2H), 4.21–4.23(m, 2H), 5.27(s,2H), 7.08(s,1H), 7.54(d,2H), 7.87(d,2H), 8.03(d, 2H), 8.21(d,2H).

IR: 1760 cm$^{-1}$ (broad).

EXAMPLE 30

[5R-[3E),5Alpha,6alpha(R*)]]-6-[1-[[(1,1-dimethylethyl) dimethylsilyl]oxy]ethyl]-7-oxo-3-[[[4-(trifluoromethyl) phenyl]sulfonyl]methylene]-1-azabicyclo[3.2.0]heptane-2-carboxylic acid, (4-nitrophenyl)methyl ester The title compound is prepared by the procedure of Example 5, using 7.0 g of product from Example 29, 75 ml anhydrous tetrahydrofuran, 11.3 ml of a 1M solution of lithium bis (trimethylsilyl) amide, 0.94 ml of acetic acid, 12.2 ml of potassium dihydrogen phosphate and 180 ml of ethyl acetate. The reaction mixture gives 6.2 g (93%) of exocyclic:endocyclic product. A 2 g aliquot is purified by chromatography to give 0.15 g (9%) of the exocyclic product as colorless crystals. A 1.5 g fraction is isolated as a mixture of exocyclic:endocyclic compound, which is reacted in Example 31.

$^1$H NMR (CDCl$_3$) δ0.07(d,6H), 0.88(s,9H), 1.24(d,3H), 2.99(m,2H), 3.80(m,1H), 4.20(t,2H), 5.27(s,1H), 5.38(s, 2H), 6.37(s,1H), 7.67(d,2H), 7.82(d,2H), 7.94(d,2H), 8.2(d, 2H).

IR: 1773, 1750 cm$^{-1}$.

EXAMPLE 31

[5R-[5Alpha,6alpha(R*)]]-6-[1-[[(1,1-dimethylethyl)-dimethylsilyl]oxy]ethyl]-7-oxo-3-[[[4-(trifluoromethyl) phenyl]sulfonyl]methyl]-1-azabicyclo[3.2.0hept-2-ene-2-carboxylic acid, (4-nitrophenyl)methyl ester One and one tenths grams of the mixture of endo and exo products from Example 30 in 60 ml of methylene chloride is treated with 5 ml of diisopropylethylamine at 5° C. for 2 days. The reaction mixture is concentrated to give 1.0 g (90%) of the desired endocyclic product.

$^1$H NMR (CDCl$_3$) δ 0.06–0.08(d,6H), 8.5(s,9H), 1.25(d, 3H), 3.22–3.25(m,2H), 4.25(m,2H), 4.36(d,1H), 4.69(d,1H), 4.97(d,1H), 5.11(d,2H), 7.26(d,2H), 7.80(d,2H), 8.18(d,2H), 8.21(d,2H).

IR: 1773, 1720 cm$^{-1}$.

EXAMPLE 32

[5R-[5Alpha,6alpha(R*)]]-6-(1-hydroxyethyl)-7-oxo-3-[[[4-(trifluoromethyl)phenyl]sulfonyl]methyl]-1-azabicyclo[3.2.0]hept-2-ene-2-carboxylic acid, (4-nitrophenyl)methyl ester The title compound is prepared by the procedure of Example 6, using 0.62 g of product from Example 31, 18ml of anhydrous tetrahydrofuran, 0.79 ml of glacial acetic acid and 4.6 ml of a 1M solution of tetra-n-butylammonium fluoride. The reaction mixture gives 0.57 g (100%) of product which is used immediately in Example 33 without further purification.

EXAMPLE 33

[5R-[5Alpha,6alpha(R*)]]-6-1-hydroxethyl)-7-oxo-3-[[4-(trifluoromethyl)phenyl]sulfonyl]methyl]-1-azabicyclo[3.2.0]hept-2-ene-2-carboxylic acid, monosodium salt A mixture of 0.57 g of product from Example 32, 20 ml of dioxane, 5 ml of water, 0.078 g of sodium bicarbonate and 0.150 g of palladium hydroxide is hydrogenated in a Parr apparatus at 21 lbs. psi for 1 hour. The reaction mixture is filtered through a pad of diatomaceous earth and the pad is washed with water and diethyl ether. The aqueous layer is extracted with 20 ml of diethyl ether and 2×20 ml of ethyl acetate. The aqueous phase is filtered through a pad of diatomaceous earth and lyophilized to give 0.255 g of a pale yellow solid. The solid is purified by reverse phase chromatography to give 0.020 g of the desired product as a white solid.

$^1$H NMR (D$_2$O) δ: 1.27(t,3H), 2.45(m,2H), 2.78(m, 1H), 4.18(m,2H), 4.48(m,3H), 7.82(d,2H), 8.06(d,2H).

EXAMPLE 34

[2R-[2-Alpha,3beta(R*)]]-3-[1-[[(1,1-dimethylethyl)-dimethylsilyl]oxy]ethyl]-2-[2-iodo-3-(2-quinolinylsulfonyl)-2-propenyl]-4-oxo-1-azetidineacetic acid, 2-chloro-2-propenyl ester A mixture of 4.205 g of 2-chloro-2-propenyl ester from Example 3, 4.52 g of sodium quinoline-2-sulfinate, 2.67 g of iodine, 2.58 g of sodium acetate in 50 ml of ethyl acetate and 50 ml of water is treated as described in Example 4 to afford 1.68 g (22%) of the desired compound.

$^1$H NMR (CDCl$_3$) δ0.06(s,6H), 0.88(s,9H), 1.24(d,3H), 3.25 (m,1H), 3.4(m, 2H), 3.85–4.25(m,6H), 4.69(s, 2H), 5.44(d,2H), 7.48(s,1H), 7.75–8.47(m,6H).

IR (neat) 1760 cm$^{-1}$ (broad peak).

EXAMPLE 35

[2R-[2Alpha,3E,5alpha,6alpha(R*)]]-6-[1-[[(1,1dimethylethyl)dimethylsilyl]oxy]ethyl]-7-oxo-3-[(2-quinolinylsulfonyl)sulfonyl)methylene]-1-azabicyclo[3.2.0]-heptane-2-carboxylic acid, 2-chloro-2-propenyl ester A solution of 1.68 g of the iodosulfone (see Example 34), in 20 ml of tetrahydrofuran is treated with 3.50 ml of a 1.0M solution of lithium bis-(trimethylsilyl)amide as described in Example 5 to afford 0.78 g (57%) of product.

$^1$H NMR (CDCl$_3$) 0.07(s,6H), 0.87(s,9H), 1.22(d,3H), 3.80(dd, 1H), 4.20(m,2H), 4.80(q,2H), 5.4(d,2H), 5.61(s, 1H), 4.85(s,1H), 7.73–8.44(m,6H).

IR (neat) 1771 cm$^{-1}$.

EXAMPLE 36

[2R-[2Alpha,3E,5alpha,6alpha(R*)]]-6-(1-hydroxyethyl)-3-[(2-quinolinylsulfonyl)methylene]-1-azabicyclo-[3.2.0]heptane-2-carboxylic acid, 2-chloro-2-propenyl ester The title compound is prepared by the procedure of Example 7, using 0.78 g of the exo compound from Example 35 and aqueous hydrogen fluoride in acetonitrile to give 0.48 g (76%) of product. The 300 Mhz nuclear magnetic resonance spectrum of this compound was essentially identical to that described in Example 35 except for the absence of the t-butyldimethylsilyl group.

EXAMPLE 37

[5R-[5Alpha,6alpha(R*)]]-6-1-hydroxyethyl)-7-oxo-3-[(2-quinolinylsulfonyl)methyl-1-azabicyclo[3.2.0]-hept-2-ene-2-carboxylic acid, 2-chloro-2-propenyl ester A solution of 0.48 g of the compound described in Example 36 in 15 ml of ethyldiisopropylamine and 15 ml of methylene chloride is treated as described in Example 8 to afford 0.33 g (69%) of product.

$^1$H NMR (CDCl$_3$) δ1.35(d,3H), 3.35(m,2H), 4.15(m, 1H), 4.4(m,2H), 4.8(dd,2H), 5.8(d,2H), 7.7–8.4(m,6H).

EXAMPLE 38

[5R-[5Alpha,6alpha(R*)]]-6-(1-hydroxyethyl)-3-[(2-quinolinylsulfonyl)methyl-7-oxo-1-azabicyclo[3.2.0]hept-2-ene-2-carboxylic acid, monopotassium salt A solution of 0.32 g of the ester (see Example 37) in 3 ml of methylene chloride is treated as described in Example 9 to afford 0.030 g of the desired compound.

$^1$H NMR (D$_6$MSO) δ1.15(d,3H), 2.65(m, 1H), 3.1(m, 1H), 3.88(m, 1H), 7.5–8.8(m,6H).

EXAMPLE 39

[2R-[2Alpha(E),3beta(R*)]]-2-(2,3-dichloro-4-methoxy-4-oxo-2-butenyl)-3-(1-hydroxyethyl)-1-4-oxo-1-azetidineacetic acid, (4-nitrophenyl)methyl ester Five and six thenths grams of the product from Example 21, 29.0 g of cupric chloride and 9.16 g of lithium chloride in 300 ml of acetonitrile is degassed and heated, under argon, at 80°–85° C. for 24 hours. The reaction mixture is concentrated in vacuo, extracted with ethyl acetate and water and dried over sodium sulfate. The resulting gum is purified by flash chromatography (ethyl acetate:hexane) to give 1.54 g (30%) of desired product.

$^1$H NMR δ1.28(d,3H), 2.15(d, 1H), 3.10(m,3H), 3.86(s, 3H), 3.89(d,1H), 4.28(m,3H), 5.27 (s,2H), 7.58(d,2H), 8.2(d,2H). CI-MS:m/z 492(M+NH$_4$)$^+$.

Identification of other column fractions yields: (a) 2.9 g (45.5%) of [2R-[2alpha(E),3(3(R*)]]-2-(2,3-dichloro-4-methoxy-4-oxo-2-butenyl)-3-[1-[[)1,1-dimethylethyl)dimethylsilyl]oxy]ethyl]-4-oxo-1-azetidineacetic acid, (4-nitrophenyl)methyl ester.

$^1$H NMR (CDCl$_3$) δ0.05(d,6H), 0.85(s,9H), 1.22(d,3H), 3.09(m,3H), 3.85(s,3H), 4.1(m,4H), 5.26(s,2H), 7.5(d,2H), 8.2(d,2H). CI-MS:m/z 606(M+NH$_4$)$^+$.

(b) 0.544 g (8.5%) of [2R-[2alpha(2),3beta(R*)]]-2-(2,3-dichloro-4-methoxy-4-oxo-2-butenyl)-3-[1-[[(1,1-dimethylethyl)dimethylsilyl]oxy]ethyl]-4-oxo-1-azetidineacetic acid, (4-nitrophenyl)methyl ester. CI-MS: m/z 606 (M+NH$_4$)$^+$; and (c) 0.212 g (4%) of [2R-[2alpha(E),3beta(R*)]]-2-(2,3-dichloro-4-methoxy-4-oxo-2-butenyl)-3-[1-[[(1,1-dimethylethyl)dimethylsilyl]oxy]ethyl]-4-oxo-1-acetidineacetic acid, (4-nitrophenyl)methyl ester. CI-MS: m/z 492 (M+NH$_4$)$^+$.

EXAMPLE 40

[2R-[2Alpha(E),3beta(R*)]]-2-(2,3-dichloro-4-methoxy-4-oxo-2-butenyl)-4-oxo-3-[1-[[(phenylmethoxy)carbonyl]oxy]ethyl]-1-azetidineacetic acid, (4-nitrophenyl)-methyl ester To a cooled, degassed solution, under argon, of 1.19 g of product from Example 39 in 20 ml of methylene chloride is added 0.478 g of benzylchloroformate and 0.342 g of 4-dimethylaminopyridine. The reaction temperature is maintained between 0°–5° C. throughout the reaction sequence. After one hour and 4 hours, 0.478.g of benzylchloroformate and 0.342 g of 4-dimethylaminopyridine is added and the reaction allowed t continue for 2 more hours (total time 6 hours). The reaction mixture is diluted with 40 ml of methylene chloride and washed with 0.5M potassium hydrogen phosphate, water and brine. The organic layer is dried over sodium sulfate, filtered and concentrated in vacuo. The resulting oil is purified by flash chromatography to give 1.06 g (70%) of the desired product.

$^1$H NMR (CDCl$_3$) δ1.43(d,2H), 3.02(m,2H), 3.22(dd,1H), 3.78(s,3H), 4.1(q,2H), 5.13(d,2H), 5.17(s,2H), 5.24(s,2H), 7.35(s,5H), 7.50(d,2H), 8.22(d,2H). CI-MS: m/z 626(M+NH$_4$)$^+$.

EXAMPLE 41

[2R-[2Alpha,3(Z),5alpha,6alpha(R*)]]-3-(1-chloro-2-methoxy-2-oxoethylidene)-7-oxo-6-[1-[[phenylmethoxy)carbonyl]oxy]ethyl-1-azabicyclo[3.2.0]-heptane-2-carboxylic acid, (4-nitrophenyl)methyl ester To a −78° C. solution, under argon, of 0.117 g of product from Example 40 in 3 ml of anhydrous tetrahydrofuran is added 0.2 ml of 1M lithium bis(trimethylsilyl)amide. The reaction temperature is maintained at −78° C. for 90 minutes followed by the addition of 0.035 ml of glacial acetic acid. The reaction mixture is treated with 1 ml of 0.5M potassium hydrogen phosphate and diluted with 20 ml of ethyl acetate. The organic layer is washed with water, brine, dried over sodium sulfate and concentrated in vacuo. The resulting oil is purified by flash chromatography ) ethyl acetate:hexane) to give 0.020 g (18%) of the desired product.

$^1$H NMR (CDCl$_3$) δ1.4 (d,3H), 2.75(m, 1H), 3.23(dd,1H), 3.35(dd,1H), 3.75(s,3H), 3.85(m, 1H), 4.97 (d,1H), 5.14(m, 1H), 5.17(s,2H), 5.32(s,2H), 7.35(s,5H), 7.6(d,2H), 8.25(d, 2H).

EXAMPLE 42

[2R-[2Alpha,3(R* or S*),5alpha,6alpha(R*)]]-α-chloro-2-[[(4-nitrophenyl)-methoxy]carbonyl]-7-oxo-6-[1-[[(phenylmethoxy)-carbonyl]oxy]ethyl]-1-azabicyclo-[3.2.0]hept-3-ene-3-acetic acid, methyl ester The title compound is prepared by the procedure of Example 41, using 0.45 g of product from Example 40, 5 ml of tetrahydrofuran, 1.6 ml of 1M sodium bis(trimethylsilyl)amide, 0.2 ml of glacial acetic acid, 10 ml of 0.5M potassium hydrogen phosphate and 20 ml ethyl acetate. The reaction mixture is purified by flash chromatography to give 0.165 g (39%) of desired product.

EXAMPLE 43

[2R-[2Alpha,3(R* or S*),5alpha,6alpha(R*)]]-3-(1-chloro-2-methoxy-2-oxoethylidene)-7-oxo-6-[1-[[(phenylmethoxy)carbonyl]-oxy]ethyl]-1-azabicyclo[ 3.2.0]heptane-2-carboxylic acid, (4-nitrophenyl)methyl ester The title compound is prepared by the procedure of Example 41, using 0.165 g of product from Example 42, 0.041 g (40 μl) of 1,8-diazobicyclo[5.4.0]-undec-7-ene, 20 ml of diethyl ether. The organic layer is concentrated in vacuo to give 0.140 g (85%) of product as a white foam.

$^1$H NMR (CDCl$_3$) δ1.4(d,3H), 2.8(m, 1H), 3.25(m,2H), 3.75(s,3H), 4.0(m, 1H), 5.15(m, 1H), 5.17(s,2H), 5.28(d, 2H), 5.68(d,1H), 7.4(s,5H), 7.5(d,2H), 8.25(d,2H).

EXAMPLE 44

(2R-[2Alpha,3(R* or S*),5alpha,6alpha(R*)]]-3-(1-chloro-2-methoxy-2-oxoethylidene)-6-(1-hydroxyethyl)-7-oxo-1-azabicyclo[3.2.0]heptane-2-carboxylic acid, monosodium salt The title compound is prepared by the procedure of Example 33, using 0.134 g of product from Example 43, 0.050 g of 10% palladium hydroxide/carbon, 0.021 g of sodium bicarbonate, 2.5 ml of dioxane and 2.5 ml of water at 40 lbs. psi for one hour. The aqueous lawyer is purified by reverse phase chromatography (water:ethanol, 95:5). The aqueous extract is lyophilized to give 0.020 g of the desired product.

$^1$H NMR (D$_2$O) δ1.38(d,3H), 3.10(m, 1H), 3.36(m,2H), 3.92(s,3H), 4.13(m, 1H), 4.33(m,2H), 5.52(s,1H).

EXAMPLE 45

[2R-[2Alpha (E),3beta(R*)]]-3-[1-[[1,1-dimethylethyl)dimethylsilyl]oxy]ethyl]-2-[3-[(4-fluorophenyl)sulfonyl]-2-iodo-2-propenyl]-4-oxo-1-azetidineacetic acid, (4-nitrophenyl)methyl ester In a similar fashion as described in Example 4, 1.1 g of the terminal acetylene prepared in Example 3A, is reacted with 0.61 g iodine and 1.05 g sodium 4-fluorophenylsulfinate to give 1.45 g of the desired product after an aqueous workup and purification.

$^1$H NMR (CDCl$_3$) δ0.07(s,3H,CH$_3$), 0.08(s,3H,CH$_3$), 0.87(s,9H,3CH$_3$), 1.25(d,3H,CH$_3$), 3.22(dd,1H,H$_3$), 3.35(dd,1H, allylic CH), 3.8(dd,1H,allylic CH), 4.05(dd,2H, CH$_2$CO$_2$), 4.2(m,2H,H$_4$+CHOSi), 5.25(s,2H,CH$_2$O), 7.25(t, 2H, aromatic), 7.5(d,2H, aromatic), 7.9(dd,2H, aromatic), 8.2(d,2H, aromatic).

IR (neat) 1760 cm$^{-1}$.

EXAMPLE 46

[2R-[2Alpha,3(E),5alpha,6alpha(R*)]]-3-[[(4-fluorophenyl)sulfonyl]methylene-6-[1-[[(1,1-dimethylethyl)-dimethyloxy]ethyl]-7-oxo-1-azabicyclo[3.2.0]-heptane-2-carboxylic acid (4-nitrophenyl)methyl ester In a similar fashion-as described in Example 5A, 1.4 g of the iodo-vinyl sulfone prepared in Example 46 is reacted with 1.3 equivalents of lithium bis(trimethylsilyl)amide at −78° C. for 1 hour to give 0.675 g of the desired product.

$^1$H NMR (CDCl$_3$) δ0.08(s,6H,2CH$_3$), 0.88(s,9H,3CH$_3$), 1.23(d,3H,CH$_3$), 2.6–3.0(m,3H,H$_6$+2H$_1$), 3.8(m, 1H,H$_5$), 4.2(p,1H,CHOSi), 5.25(s,1H,H$_3$), 5.4(s,2H,CH$_2$O), 6.35(s, 1H,vinyl), 7.2(t,2H,aromatic), 7.68(d,2H,aromatic), 7.8(dd, 2H, aromatic), 8.2(d,2H, aromatic).

IR (KBr)–1765, 1745 cm$^{-1}$.

EXAMPLE 47

[5R-[5Alpha,6alpha(R*)]]-3-[[4-fluorophenyl)-sulfonyl]methyl-6-(1-hydroxyethyl)-7-oxo-1-azabicyclo[3.2.0]hept-2-ene-2-carboxylic acid, (4-nitrophenyl)methyl ester In a similar fashion as described in Example 7, 0.25 g of the exocyclic carbapenem prepared in Example 46 is reacted with hydrogen fluoride dissolved in acetonitrile to give the exo-6-(1-hydroxyethyl) derivative which is carried on into the diisopropylethylamine isomerization step in similar fashion as described in Example 8 to give 0.138 g desired product.

$^1$H NMR (CDCl$_3$)–1.35(d,3H,CH$_3$), 3.15(dd, 1H,H$_1$), 3.3(dd,1H,H$_6$), 3.35(dd, 1H,H$_1$), 4.3(m,2H,H$_5$ and CHO), 4.52 (dd,2H, CH$_2$S), 5.15(dd,2H, CH$_2$O), 7.15 (t, 2H, aromatic), 7.55(d,2H,aromatic), 7.85(dd,2H,aromatic), 8.23 (d, 2H, aromatic).

IR (KBr)–3534, 1782, 1717 cm$^{-1}$.

EXAMPLE 48

[5R-[5Alpha,6alpha(R*)]]3-[[fluorophenyl)sulfonyl]-methyl]-6-(1-hydroxyethyl)-7-oxo-1-azabicyclo-[3.2.0]hept-2-ene-2-carboxylic acid, monosodium salt In a similar fashion to that described in Example 33, 0.173 g of the carbapenem prepared in Example 47 is reacted with hydrogen (2 atmospheres pressure) and 0.059 g palladium hydroxide catalyst for 0.75 hour to give 0.12 g desired product.

$^1$H NMR (D$_2$O)–1.3(d,3H, CH$_3$), 3.05(dddd, 2H, allylic CH$_2$), 3.4(dd,1H,H$_6$), 4.17(m,2H,CHO and H$_5$), 4.65(dd,2H, CH$_2$S), 7.4(t,2H,aromatic), 7.4(dd,2H,aromatic).

IR (KBr)–3470 (broad), 1740, 1667, 1600 cm$^{-1}$.

EXAMPLE 49

[2R-[2Alpha,3beta(R*)]]-2-[4-(4-bromophenyl)-4-hydroxy-2-butynyl]-3-[1[[(1,1-dimethylethyl)dimethyl-silyl]oxy]-4-oxo-1-azetidineacetic acid, diphenylmethyl ester To a −78° C. solution, under argon, of 0.3 g of product from Example 2 in 4.5 ml of dry tetrahydrofuran is added dropwise, with stirring, 1.2 ml of 1.6M n-butyllithium. After 1 hour, a solution of 0.205 g p-bromobenzaldehyde in 0.4 ml tetrahydrofuran is added and the reaction is stirred for 45 minutes at −78° C. The cooling bath is allowed to warm to −50° C. at which time the reaction is quenched with 1 ml of saturated ammonium chloride. The cooling bath is removed and the mixture is diluted with ethyl acetate, water and 0.05 ml of glacial acetic acid. After vigorous stirring, the mixture is partitioned and the organic layer washed with water and brine. The organic layer is dried over magnesium sulfate, filtered and concentrated in vacuo.

The crude product is dissolved in 3 ml of tetrahydrofuran and treated with 0.18 g of solid diphenyldiazomethane. After the visible signs of nitrogen evolution have ceased, the reaction is warmed to 60° C. for 45 minutes. The mixture is cooled to room temperature, concentrated in vacuo and chromatographed on silica gel with 20% ethyl acetate/hexane to give 0.174 g (28%) of the desired product.

$^1$H NMR (CDCl$_3$) δ0.03(d,6H), 0.82(s,9H), 1.2(d,3H), 2.4–2.65(m,3H), 2.85(m,1H), 3.9(m,1H), 4.1(m,3H), 5.18(m,1H), 6.9(d,1H), 7.2–7.4(m,14H).

EXAMPLE 50

[2R-2Alpha,3beta(R*)]-2-[4(4-bromophenyl)-4-oxo-2-butynyl]-3-[1-[[(1,1-dimethylethyl)dimethylsilyl]oxy]-ethyl]-4-oxo-1-azetidineacetic acid, diphenylmethyl ester A solution of 0.106 g of the product from Example 49 in 5 ml of methylene chloride is combined with 1 g of diatomaceous earth followed by 0.104 g of pyridinium chlorochromate. After stirring for 15 hours, the reaction is diluted with 3 ml of 50% ethyl acetate/hexane and filtered through silica gel rinsing with 50% ethyl acetate/hexane and ethyl acetate. The filtrate is concentrated in vacuo to give 0.087 g (80%) of the desired product as a yellow oil/foam.

$^1$H NMR (CDCl$_3$) δ0.05(d,6H), 0.85(s,9H), 1.25(d,3H), 2.88 (m,2H), 3.05(m,1H), 4.08(m, 1H), 4.18(s, 2H), 4.2(m, 1H), 6.85(s,1H), 7.3(m,10H), 7.6(d,2H), 7.9(d,2H).

EXAMPLE 51

[2R-[2Alpha(E),3beta(R*)]]-2-[4-(4-bromophenyl)-2-iodo-4-oxo-2-butenyl]-3-[1-[[(1,1-dimethylethyl)-dimethylsilyl]oxy]ethyl]-4-oxo-1-azetidineacetic acid, diphenylmethyl ester To a −78° C. solution, under argon, of 0.087 g of the product from Example 50 in 2 ml of methylene chloride is added 0.037 ml of trimethylsilyliodide. After 20 minutes, the reaction is quenched with 1 ml of 50% diethylether/water. The mixture is diluted with methylene chloride/water, partitioned and the organic layer is washed with saturated sodium bicarbonate and brine. The organic layer is dried over magnesium sulfate, filtered, and concentrated in vacuo. The residue is chromatographed on silica gel with 20% ethyl acetate/hexane to give 0.059 g (57%) of the desired product as a yellow foam.

¹H NMR (CDCl₃) 0.08(d,6H), 0.85(s,9H), 1.25(d,3H), 2.95(m,1H), 3.0–3.2(m,2H), 4.1(q,2H), 4.1(q,2H), 4.18–4.3(m,2H), 6.85(s,1H), 7.3(m,10H), 7.6(d,2H), 7.75(d, 2H).

EXAMPLE 52

[5R-[5Alpha, 6alpha (R*)]]-3-[2-(4-bromophenyl)-2-oxoethyl]-6-[1-[[(1,1-dimethylethyl)dimethylsilyl]oxy]ethyl]-7-oxo-1-azabicyclo[3.2.0]hept-2-ene-2-carboxylic acid, diphenylmethyl ester To a −78° C. solution, under argon, of 0.059 g of product from Example 51 in 2 ml of tetrahydrofuran is added 0.088 ml of 1M lithium bis(trimethylsilyl)amide. After 15 minutes, an additional 0.073 ml of 1M lithium bis(trimethylsilyl)amide is added and the reaction stirred for 15 minutes at −78° C. The reaction is quenched with saturated aqueous ammonium chloride, diluted with ethyl acetate and washed with water and brine. The organic layer is dried over magnesium sulfate, concentrated in vacuo and chromatographed on silica gel with 10% ethyl acetate/hexane to give 0.010 g (20%) of the bicyclic endocyclic product.

¹H NMR (CDCl₃) δ0.1(d,6H), 0.9(s,9H), 1.25(d,3H), 2.82–3.05(m,2H), 3.18(m, 1H), 4.15(d, 1H), 4.25(m,2H), 4.5(d,1H), 6.85(s,1H), 7.2–7.45(m,8H), 7.55(m,4H), 7.8(d, 2H).

IR (neat) 1776, 1711 cm⁻¹.

EXAMPLES 53 to 113

EXAMPLES 53 to 113 describe compounds of Formula LXII which are obtained by the methodology described hereinabove.

TABLE 3

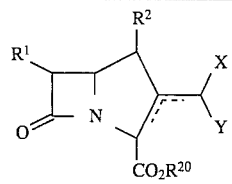

LXII

| Example | R¹ | R² | R²⁰ | Y | X | Double Bond Position |
|---|---|---|---|---|---|---|
| 53 | CH₃CH(OH)— | H | Na | 4-fluorobenzene sulfonyl | I | exo |
| 54 | CH₃CH(OH)— | H | POM | CO₂Na | Cl | endo |
| 55 | CH₃CH(OH)— | H | POM | CO₂Na | H | endo |
| 56 | CH₃CH(OH)— | H | POM | CON(CH₃)₂ | Cl | endo |
| 57 | CH₃CH(OH)— | H | POM | CON(CH₃)₂ | Cl | exo |
| 58 | CH₃CH(OH)— | H | POM | CON(CH₃)₂ | H | exo |
| 59 | CH₃CH(OH)— | H | POM | CON(CH₃)₂ | H | endo |
| 60 | CH₃CH(OH)— | H | POM | CONH₂ | Cl | exo |
| 61 | CH₃CH(OH)— | H | POM | CN | Cl | exo |
| 62 | CH₃CH(OH)— | H | POM | CN | Cl | endo |
| 63 | CH₃CH(OH)— | H | POM | NO₂ | Cl | exo |
| 64 | CH₃CH(OH)— | H | POM | C(O)-1-piperazinyl | Cl | exo |
| 65 | CH₃CH(OH)— | H | POM | C(O)-1-piperazinyl | H | endo |
| 66 | CH₃CH(OH)— | H | POM | C(O)-1-piperazinyl | Cl | endo |
| 67 | CH₃CH(OH)— | H | POM | CO-(4-bromophenyl) | Cl | exo |
| 68 | CH₃CH(OH)— | H | POM | CO-(4-bromophenyl) | Cl | endo |
| 69 | CH₃CH(OH)— | H | POM | CO-(4-bromophenyl) | H | endo |
| 70 | CH₃CH(OH)— | H | POM | C(S)N(CH₃)₂ | Cl | exo |
| 71 | CH₃CH(OH)— | H | POM | C(S)N(CH₃)₂ | Cl | endo |
| 72 | CH₃CH(OH)— | H | POM | C(S)N(CH₃)₂ | H | endo |
| 73 | CH₃CH(OH)— | H | POM | C(S)OCH₃ | Cl | exo |
| 74 | CH₃CH(OH)— | H | POM | C(S)OCH₃ | Cl | endo |
| 75 | CH₃CH(OH)— | H | POM | C(S)OCH₃ | H | endo |
| 76 | CH₃CH(OH)— | H | POM | C(S)-1-piperazinyl | Cl | exo |
| 77 | CH₃CH(OH)— | H | POM | C(S)-1-piperazinyl | Cl | endo |
| 78 | CH₃CH(OH)— | H | POM | C(S)-1-piperazinyl | H | endo |
| 79 | CH₃CH(OH)— | H | POM | C(S)SCH₃ | Cl | exo |
| 80 | CH₃CH(OH)— | H | POM | C(S)SCH₃ | Cl | endo |
| 81 | CH₃CH(OH)— | H | POM | C(S)SCH₃ | H | endo |
| 82 | CH₃CH(OH)— | H | POM | C(O)NHCH₃ | Cl | exo |
| 83 | CH₃CH(OH)— | H | POM | C(O)NHCH₃ | Cl | endo |
| 84 | CH₃CH(OH)— | H | POM | C(O)NHCH₃ | H | endo |
| 85 | CH₃CH(OH)— | H | POM | 4-(fluoro)thiophenyl | Cl | exo |
| 86 | CH₃CH(OH)— | H | POM | 4-(fluoro)thiophenyl | Cl | endo |
| 87 | CH₃CH(OH)— | H | POM | S(O)-4-fluorophenyl | Cl | exo |
| 88 | CH₃CH(OH)— | H | POM | S(O)-4-fluorophenyl | Cl | endo |
| 89 | CH₃CH(OH)— | H | POM | CN | I | exo |
| 90 | CH₃CH(OH)— | H | POM | CN | F | exo |
| 91 | CH₃CH(OH)— | H | POM | CN | F | endo |
| 92 | CH₃CH(OH)— | H | POM | CO₂Na | F | exo |
| 93 | CH₃CH(OH)— | H | POM | CO₂Na | F | endo |
| 94 | CH₃CH(OH)— | H | POM | CO₂Na | Br | exo |
| 95 | CH₃CH(OH)— | H | POM | CO₂CH₃ | F | exo |
| 96 | CH₃CH(OH)— | H | POM | C(O)-1-piperazinyl | Br | exo |
| 97 | CH₃CH(OH)— | H | POM | C(O)-1-piperazinyl | Br | endo |

TABLE 3-continued

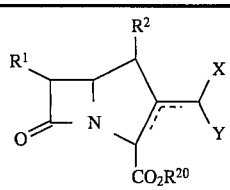

LXII

| Example | R¹ | R² | R²⁰ | Y | X | Double Bond Position |
|---|---|---|---|---|---|---|
| 98 | CH₃CH(OH)— | H | POM | C(O)-1-piperazinyl | F | exo |
| 99 | CH₃CH(OH)— | H | POM | C(O)-1-piperazinyl | F | endo |
| 100 | CH₃CH(OH)— | H | POM | C(O)-2-pyridyl | Cl | exo |
| 101 | CH₃CH(OH)— | H | POM | C(O)-2-pyridyl | Cl | endo |
| 102 | CH₃CH(OH)— | H | POM | C(O)-2-pyridyl | Br | exo |
| 103 | CH₃CH(OH)— | H | POM | C(O)-2-thienyl | Cl | endo |
| 104 | CH₃CH(OH)— | H | POM | C(O)-(1-methyl-imidazol-2-yl) | Cl | endo |
| 105 | CH₃CH(OH)— | H | POM | C(O)-2-thiazolyl | Cl | endo |
| 106 | CH₃CH(OH)— | H | POM | C(O)-2-oxazolyl | Cl | endo |
| 107 | CH₃CH(OH)— | H | POM | C(O)-(1-methyl-pyrrol-2-yl) | Br | endo |
| 108 | CH₃CH(OH)— | H | POM | C(O)N(CH₃)₂ | Br | endo |
| 109 | CH₃CH(OH)— | H | POM | C(O)N(CH₃)₂ | Br | endo |
| 110 | CH₃CH(OH)— | H | POM | C(S)-H-thiomorpholinyl | Cl | exo |
| 111 | CH₃CH(OH)— | H | POM | C(S)-H-thiomorpholinyl | Cl | endo |
| 112 | CH₃CH(OH)— | H | POM | C(S)-H-thiomorpholinyl | Br | endo |
| 113 | CH₃CH(OH)— | H | POM | C(S)-H-thiomorpholinyl | H | endo |

POM = pivaloyloxymethyl

We claim:

1. A substituted allylazetidione compound having the formula:

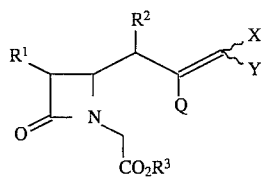

wherein

R¹ is hydrogen; a straight-chain or branched lower alkyl group selected from methyl, ethyl, n-propyl, isopropyl, n-butyl, isobutyl, sec-butyl, tert-butyl, n-pentyl, or isopentyl; a straight-chained or branched lower alkoxy group selected from methoxy, ethoxy, n-propoxy, isopropoxy, n-butoxy, isobutoxy, sec-butoxy, or tert-butoxy; or a $R^4$ B group wherein $R^4$ is hydroxyl; a lower alkoxy group selected from methoxy, ethoxy, n-propoxy, or isopropoxy; fluoride; an acyloxy group selected from acetoxy, propionyloxy, n-butyryloxy, or isobutyryloxy or an aralkyloxycarbonyloxy group selected from benzyloxycarbonyloxy or p-nitrobenzyloxycarbonyloxy; a lower alkylsulfonyloxy group elected from methanesulfonyloxy, ethanesulfonyloxy, or propanesulfonyloxy; an arylsulfonyloxy group selected from benzenesulfonyloxy or p-toluenesulfonyloxy; a lower trialkylsilyloxy group selected from trimethylsilyloxy or tert-butyldimethylsilyloxy; mercapto; a lower alkylthio group selected from methylthio, ethylthio, n-propylthio, or isopropylthio; amino ; or a lower aliphatic acylamino group selected from acetylamino, propionylamino, n-butyrylamino, or isobutyrylamino; and B is selected from methylene, ethylene, ethylidene, trimethylene, propylidene, isopropylidene, tetramethylene, butylidene, pentamethylene, pentylidene, 2,2,2-trifluoroethylidene, 3,3,3-trifluoropropylidene, or benzylidene;

$R^2$=hydrogen, $C_1$-$C_6$ alkyl, phenyl and substituted phenyl, the substituents selected from $C_1$-$C_6$ alkyl;

$R^3$ is hydrogen; a straight-chain or branched lower alkyl group selected from methyl, ethyl, n-propyl, isopropyl, n-butyl, isobutyl, or tert-butyl; a lower haloalkyl group selected from 2-iodoethyl, 2,2-dibromoethyl, or 2,2,2-trichloroethyl; a lower alkoxymethyl group selected from methoxymethyl, ethoxymethyl, n-propoxymethyl, isopropoxymethyl, n-butoxymethyl, or isobutoxymethyl; a lower aliphatic acyloxymethyl group selected from acetoxymethyl, propionyloxymethyl, n-butyryloxymethyl, isobutyryloxymethyl, or pivaloyloxymethyl; a 1-(lower alkoxy)carbonyloxyethyl group selected from 1-methoxycarbonyloxyethyl, 1-ethoxycarbonyloxyethyl, 1-n-propoxycarbonyloxyethyl, 1-isopropoxycarbonyloxyethyl, 1-n-butoxycarbonyloxy-ethyl, or 1-isobutoxycarbonyloxyethyl; an aralkyl group selected from benzyl, p-methoxybenzyl, o-nitrobenzyl, or p-nitrobenzyl; benzhydryl; phthalidyl; a silyl group selected from trimethylsilyl or t-butyldimethylsilyl or 2-trimethylsilylethyl; an allylic group selected from allyl, 2-chloro-2-propenyl, 2-butenyl, 3-methyl-2-butenyl or 2-cinnamyl;

Q=a suitable leaving group selected from the group consisting of:

F, Cl, Br, I, $R^{21}$S, $R^{21}SO_2$,[$NR^{21}{}_3$, $PR^{21}{}_3$,] $OR^{21}$, $OCOR^2$, OOH, $OOR^{21}$, —OP(O) (OPh)$_2$, —OP(O) (OCCl$_3$)$_2$, —OSO$_2$(4–OSO$_2$(4-nitrophenyl), —OSO$_2$CH$_3$ and CN;

$R^{21}$=a straight or branched chain alkyl having 1–10 carbon atoms; a phenyl-substituted alkyl group selected from benzyl, benzhydryl CH(C$_6$H$_6$)$_2$, 2-phenylethyl; phenyl, optionally substituted by 1–3 substituents independently selected from fluoro, chloro, bromo, $C_{1-C3}$ alkyl, SO$_2$, $R^{17}$, CO$_2$, $R^{16}$, CONR$^{18}$, $R^{19}$;

X=fluorine, chlorine, bromine, iodine, hydrogen;

Y=a suitable electron withdrawing group selected from the group consisting of

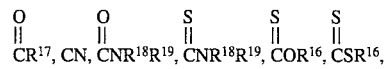

F, Cl, Br, I;

$R^{16}$=a straight-chain or branched lower alkyl group selected from methyl, ethyl, n-propyl, isopropyl, n-butyl, isobutyl; a lower haloalkyl group selected from 2-chloroethyl, 3-chloropropyl, 2-iodoethyl, 2,2-dibromoethyl or 2,2,2-trichloroethyl; a lower trimethylsilylalkyl group selected from 2-trimethylsilylethyl; substituted allyl group selected from 2-chloro-2-propenyl, 3-methyl-2-propenyl, 3-methyl-2-butenyl, 3-phenyl-2-propenyl; a lower alkyl-t-butyldimethylsiloxy group selected from 2-(t-butyldimethylsiloxy) ethyl or 2-(t-butyldimethylsiloxy) propyl; a lower alkyl-hydroxy group of 2–4 carbon atoms selected from 2-hydroxyethyl, 3-hydroxylpropyl or 3-hydroxy-n-butyl; phenyl; an alkylheterocycle group with the alkyl moiety having 1–3 carbon atoms attached to a 5- or 6-membered ring that contains 1–4 O, N or S atoms through a ring carbon or ring nitrogen;

$R^{17}$=1) phenyl, optionally substituted by 1–3 substituents independently selected from: 1a) halogens (F, Cl, Br, I) and/or trifluoromethyl; 1b) $C_1$-$C_4$ branched or linear alkyl; 1c) hydroxy or a protected hydroxy group, amino or a protected amino group, thiol or a protected thiol group; 1d) an alkenyl or alkynyl group having 1–4 carbon atoms selected from ethenyl, 1-propenyl, 2-propenyl, 3-propenyl, ethynyl, 1-proynyl; 1e) carboxy or carboxamido 1f) a heterocycle group that contains 1–4 O , N or S atoms attached through a ring carbon or nitrogen;

$R^{18}$ and $R^{19}$ are independently selected from hydrogen; alkyl having from 1–10 carbon atoms; cycloalkyl having from 1–10 carbon atoms; phenyl alkyl and heterocycloalkyl wherein the alkyl has 1–6 carbon atoms and the heteroatom or atoms are selected from O, N and S.

2. The compound according to claim 1, [2R-[2Alpha[E],3beta(R*)]]-2[3-[(2,4-difluorophenyl)sulfonyl]-3-iodo-2-propenyl]-3-[1-[[(1,1-dimethylethyl)dimethylsilyl]oxy] ethyl]-4-oxo-1-azetidineacetic acid, 2-chloro-2-propenyl ester.

3. The compound according to claim 1, [2R-[2Alpha(E),3beta(R*)]]-2[3-[(3,4-dimethoxyphenyl)sulfonyl]- 2-iodo-2-propenyl]-3-[1-[[(1,1-dimethylethyl)dimethylsilyl]oxy] ethyl]-4-oxo-1-azetidineacetic acid, 2-chloro-2-propenyl ester.

4. The compound according to claim 1, [2R-[2Alpha(E),3beta(R*)]]-3-[1-[[(1,1-dimethylethyl)dimethylsilyl]oxy] ethyl]-2[3-[[4-(1,1dimethylethyl)phenyl]sulfonyl]-2-iodo-2-propenyl-4-oxo-1-azetidineacetic acid, 2-chloro-2-propenyl ester.

5. The compound according to claim 1, [2R-[2Alpha(e),3beta(R*)]]-3-[1-[[(1,1-dimethylethyl)dimethylsilyl]oxy]

ethyl]-2-[2-iodo-3-(2-thienylsulfonyl)-2-propenyl]-4-oxo-1-azetidineacetic acid, (4-nitrophenyl)methyl ester.

6. The compound according to claim 1, [2R-[2Alpha(E), 3beta(R*)]]-3-[1-[[(1,1-dimethylethyl)dimethylsilyl]oxy]ethyl]-2-[2-iodo-3-[(4-methylphenyl)sulfonyl]-2-propenyl]-4-oxo-1-azetidineacetic acid, (4-methoxyphenyl)methyl ester.

7. The compound according to claim 1, [2R-[2Alpha(E), 3beta(R*)]]-2-[3-[[4-(acetylamino)phenyl]sulfonyl]-2-iodo-2-propenyl]-3-[1-[[1,1-dimethylethyl)dimethylsilyl]oxy]ethyl]-4-oxo-1-azetidineacetic acid, 2-chloro-2-propenyl ester.

8. The compound according to claim 1, [2R-[2Alpha(E), 3beta(R*)]]-2-(2,3-dichloro-4-methoxy-4-oxo-2-butenyl)-3-[1-[[1,1-dimethylethyl)dimethylsilyl]oxy]ethyl]-4-oxo-1-azetidineacetic acid, (4-nitrophenyl)methyl ester.

9. The compound according to claim 1, [2R-[2Alpha(E), 3beta(R*)]]-3-[1-[[(1,1-dimethylethyl)-dimethylsilyl]oxy]ethyl]- 2-[2-iodo-3-(phenylsulfonyl)-2-propenyl]-4-oxo-1-azetidineacetic acid, (4-methoxyphenyl)methyl ester.

10. The compound according to claim 1, [2R-[2Alpha(Z), 3beta(R*)]]-3-[1-[[(1,1dimethylethyl)dimethylsilyl]oxy]ethyl]-2-[2-iodo-3-[[4-(trifluoromethyl)phenyl]sulfonyl]-2-propenyl]-4-oxo-1-azetidineacetic acid, (4-nitrophenyl)methyl ester.

11. The compound according to claim 1, [2R-[2Alpha, 3beta(R*)]]-3-[1-[[(1,1-dimethylethyl)dimethylsilyl]oxy]ethyl]-2-[2-iodo-3-(2-quinolinylsulfonyl)-2-propenyl]-4-oxo-1-azetidineacetic acid, 2-chloro-2-propenyl ester.

12. The compound according to claim 1, [2R-[2Alpha(E), 3beta(R*)]]-2-(2,3-dichloro-4-methoxy-4-oxo-2-butenyl)-3-(1-hydroxyethyl)-4-oxo-1azetidineacetic acid, (4-nitrophenyl)methyl ester.

13. The compound according to claim 1, [2R-[2Alpha(E), 3beta(R*)]]-2-(2,3-dichloro-4-methoxy-4-oxo- 2-butenyl)-4-oxo-3-[1-]](phenylmethoxy)carbonyl]oxy]ethyl]-1-azetidineacetic acid, (4-nitrophenyl)methyl ester.

14. The compound according to claim 1, [2R-[2Alpha(E), 3beta(R*)]]-3-[1-[[1,1-dimethylethyl)dimethylsilyl]oxy]ethyl-2-[3-[(4-fluorophenyl)sulfonyl]-2-iodo-2-propenyl]-4-oxo-1-azetidineacetic acid, (4-nitrophenyl)methyl ester.

15. The compound according to claim 1, [2R-[2Alpha(E), 3beta(R*)]]-2-[4-(4-bromophenyl)-2-iodo-4-oxo-2-butenyl]-3-[1-[[(1,1-dimethylethyl)dimethylsilyl]oxy]ethyl]- 4-oxo-1-azetidineacetic acid, diphenylmethyl ester.

16. A propargyl azetidinone compound having the formula:

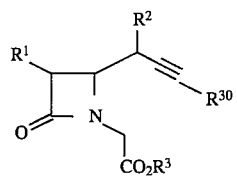

wherein

R¹ is hydrogen; straight-chain or branched lower alkyl group selected from methyl, ethyl, n-propyl, isopropyl, n-butyl, isobutyl, sec-butyl, tert-butyl, n-pentyl, or isopentyl; a straight-chained or branched lower alkoxy group selected from methoxy, ethoxy, n-propoxy, isopropoxy, n-butoxy, isobutoxy, sec-butoxy, or tert-butoxy; or a $R^4$ B group wherein $R^4$ is hydroxyl; a lower alkoxy group selected from methoxy, ethoxy, n-propoxy, or isopropoxy; fluoride; an acyloxy group selected from acetoxy, propionyloxy, n-butyryloxy, or isobutyryloxy or an aralkyloxycarbonyloxy group selected from benzyloxycarbonyloxy or p-nitrobenzyloxycarbonyloxy; a lower alkylsulfonyloxy group selected from methanesulfonyloxy, ethanesulfonyloxy, or propanesulfonyloxy; an arylsulfonyloxy group selected from benzenesulfonyloxy or p-toluenesulfonyloxy; a lower trialkylsilyloxy group selected from trimethylsilyloxy or tert-butyldimethylsilyloxy; mercapto; a lower alkylthio group selected from methylthio, ethylthio, n-propylthio, or isopropylthio; amino; or a lower aliphatic acylamino group selected from acetylamino, propionylamino, n-butyrylamino, or isobutyrylamino; and B is selected from methylene, ethylene, ethylidene, trimethylene, propylidene, isopropylidene, tetramethylene, butylidene, pentamethylene, pentylidene, 2,2,2-trifluoroethylidene, 3,3,3-trifluoropropylidene, or benzylidene;

$R^2$=hydrogen, $C_1$–$C_6$ alkyl, phenyl and substituted phenyl, the substituents selected from $C_1$–$C_6$ alkyl;

$R^3$ is hydrogen; a straight-chain or branched lower alkyl group selected from methyl, ethyl, n-propyl, isopropyl, n-butyl, isobutyl, or tert-butyl; a lower haloalkyl group selected from 2-iodoethyl, 2,2-dibromoethyl, or 2,2,2-trichloroethyl; a lower alkoxymethyl group selected from methoxymethyl, ethoxymethyl, n-propoxymethyl, isopropoxymethyl, n-butoxymethyl, or isobutoxymethyl; a lower aliphatic acyloxymethyl group selected from acetoxymethyl, propionyloxymethyl, n-butyryloxymethyl, isobutyryloxymethyl, or pivaloyloxymethyl; a 1-(lower alkoxy) carbonyloxyethyl group selected from 1-methoxycarbonyloxyethyl, 1-ethoxycarbonyloxyethyl, 1-n-propoxycarbonyloxyethyl, 1-isopropoxycarbonyloxyethyl, 1-n-butoxycarbonyloxyethyl, or 1-isobutoxycarbonyloxyethyl; an aralkyl group selected from benzyl, p-methoxybenzyl, o-nitrobenzyl, or p-nitrobenzyl; benzhydryl; phthalidyl; a silyl group selected from trimethylsilyl or t-butyldimethylsilyl or 2-trimethylsilylethyl; an allylic group selected from allyl, 2-chloro-2-propenyl, 2-butenyl, 3-methyl-2-butenyl or 2-cinnamyl; or a water soluble cation selected from lithium, sodium, potassium, ammonium or tetraalkyl ammonium (alkyl of $C_1$–$C_4$);

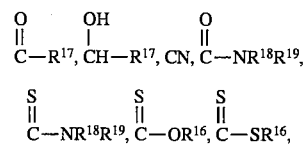

$SO_2$, $R^{17}$, $SOR^{17}$, $SR^{17}$, F, Cl, Br, I, trimethylsilyl;

$R^{16}$=a straight-chain or branched lower alkyl group selected from methyl, ethyl, n-propyl, isopropyl, n-butyl, isobutyl; a lower haloalkyl group selected from 2-chloroethyl, 3-chloropropyl, 2-iodoethyl, 2,2-dibromoethyl or 2,2,2-trichloroethyl; a lower trimethylsilylalkyl group selected from 2-trimethylsilylethyl; substituted allyl group selected from 2-chloro-2-propenyl, 3-methyl-2-propenyl, 3-methyl-2-butenyl, 3-phenyl-2-propenyl; a lower alkyl-t-butyldimethylsiloxy group selected from 2-(t-butyldimethylsiloxy) ethyl or 2-(t-butyldimethylsiloxy) propyl; a lower alkyl-hydroxy group of 2–4 carbon atoms selected from 2-hydroxyethyl, 3-hydroxylpropyl or 3-hydroxy-n-butyl; phenyl; an alkylheterocycle group with the alkyl moiety having 1–3 carbon atoms attached to a 5- or 6-membered ring that contains 1–4 O , N or S atoms through a ring carbon or ring nitrogen;

$R^{17}$=1) phenyl , optionally substituted by 1–3 substituents independently selected from: 1a) halogens (F, Cl, Br, I)

and/or trifluoromethyl; 1b) $C_1$–$C_4$ branched or linear alkyl; 1c) hydroxy or a protected hydroxy group, amino or a protected amino group, thiol or protected a thiol group; 1d) an alkenyl or alkynyl group having 1–4 carbon atoms selected from ethenyl, 1-propenyl, 2-propenyl, 3-propenyl, ethynyl, 1-proynyl; 1e) carboxy or carboxamido 1f) a heterocycle group that contains 1–4 O, N or S atoms attached through a ring carbon or nitrogen;

$R^{18}$ and $R^{19}$ are independently selected from hydrogen; alkyl having from 1–10 carbon atoms; cycloalkyl having from 1–10 carbon atoms; phenyl alkyl and heterocycloalkyl wherein the alkyl has 1–6 carbon atoms and the heteroatom or atoms are selected from O, N and S.

17. The compound according to claim 16, [3S-[3Alpha(S*),4beta]]-3-[1-[[1,1-dimethylethyl)dimethylsilyl] oxy]ethyl]- 2-oxo-4-[2-propynyl-1-azetidineacetic acid.

18. The compound according to claim 16, [3S-[3Alpha(S*),4beta]]-3-[1-[[(1,1-dimethylethyl)dimethylsilyl] oxy]ethyl]- 2-oxo-4-(2-propynyl)-1-azetidineacetic acid, 2-chloro-2-propenyl ester.

19. The compound according to claim 16, [3S-[3Alpha(S*),4beta]]-3-[1-[[(1,1-dimethylethyl)dimethylsilyl] oxy]ethyl]- 2-oxo-3-(2-propynyl)-1-azetidineacetic acid, (4-nitrophenyl)methyl ester.

20. The compound according to claim 16, [2R-[2Alpha,3beta(R*)]]-3-[1-[[1,1-dimethyl)dimethylsilyloxy]ethyl]-2-(4-methoxy-4-oxo-2-butynyl)-4-oxo-1-azetidineacetic acid, (4-nitrophenyl)methyl ester.

21. The compound according to claim 16, [3S-[3Alpha(S*),4beta]]-3-[1-[[1,1-dimethylethyl)dimethylsilyl] oxy]ethyl]- 2-oxo-4-(2-propynyl)-1-azetidineacetic acid, (4-methoxyphenyl)methyl ester.

22. The compound according to claim 16, [2R-[2Alpha,3beta(R*)]]-2-[4-(4-bromophenyl)-4-hydroxy- 2-butynyl]-3-[1-[[(1,1-dimethylethyl)dimethylsilyl]oxy]- 4-oxo-1-azetidineacetic acid, diphenylmethyl ester.

23. The compound according to claim 16, [2R-[2Alpha,3beta(R*)]]-2-[4-(4-bromophenyl)-4-oxo-2-butynyl]-3-[1-[[(1,1-dimethylethyl)dimethylsilyl]oxy]ethyl]-4-oxo-1-azetidineacetic acid, diphenylmethyl ester.

* * * * *